(12) United States Patent
Bova et al.

(10) Patent No.: US 12,123,060 B2
(45) Date of Patent: Oct. 22, 2024

(54) METHOD FOR IDENTIFYING TARGETS FOR PRECISION CANCER THERAPY

(71) Applicant: Tampere University Foundation sr, Tampere University (FI)

(72) Inventors: George Steven Bova, Tampere University (FI); Matti Nykter, Tampere University (FI)

(73) Assignee: Tampere University Foundation sr, Tampere University (FI)

(*) Notice: Subject to any disclaimer, the term of this patent is extended or adjusted under 35 U.S.C. 154(b) by 16 days.

(21) Appl. No.: 17/495,468

(22) Filed: Oct. 6, 2021

(65) Prior Publication Data

US 2023/0104563 A1 Apr. 6, 2023

(51) Int. Cl.
*C12Q 1/6886* (2018.01)

(52) U.S. Cl.
CPC ..... *C12Q 1/6886* (2013.01); *C12Q 2600/158* (2013.01); *C12Q 2600/178* (2013.01)

(58) Field of Classification Search
None
See application file for complete search history.

(56) References Cited

FOREIGN PATENT DOCUMENTS

WO WO-2016048952 A1 * 3/2016 ........... C12Q 1/6858

OTHER PUBLICATIONS

Ma et al. Rise and fall of subclones from diagnosis to relapse in pediatric B-acute lymphoblastic leukaemia. Nature Communications. 2015; 6:6604.
Woodcock DJ, Riabchenko E, Taavitsainen S, Kankainen M, Gundem G, Brewer DS, et al. Prostate cancer evolution from multilineage primary to single lineage metastases with implications for liquid biopsy. Nature Communications. 2020; 11:5070.
Tubio et al. Mobile DNA in cancer. Extensive transduction of nonrepetitive DNA mediated by L1 retrotransposition in cancer genomes. Science. 2014; 345:1251343.
Ketola et al. Subclone Eradication Analysis Identifies Targets for Enhanced Cancer Therapy and Reveals L1 Retrotransposition as a Dynamic Source of Cancer Heterogeneity. Cancer Research Online First; doi: 10.1158/0008-5472.CAN-21-0371.
Kimberland ML, Divoky V, Prchal J, Schwahn U, Berger W, Kazazian HH. Full-length human L1 insertions retain the capacity for high frequency retrotransposition in cultured cells. Hum Mol Genet. 1999;8:1557-60.
Ostertag EM, Kazazian HH. Twin Priming: A Proposed Mechanism for the Creation of Inversions in L1 Retrotransposition. Genome Res. 2001;11:2059-65.
Faulkner GJ, Billon V. L1 retrotransposition in the soma: a field jumping ahead. Mobile DNA. 2018;9:22.
Liao Y, Smyth GK, Shi W. featureCounts: an efficient general purpose program for assigning sequence reads to genomic features. Bioinformatics. 2014;30:923-30.
Gundem G, Van Loo P, Kremeyer B, Alexandrov LB, Tubio JMC, Papaemmanuil E, et al. The evolutionary history of ethal metastatic prostate cancer. Nature. 2015;520:353-7.
Pomerantz MM, Spisák S, Jia L, Cronin AM, Csabai I, Ledet E, et al. The association between germline BRCA2 variants and sensitivity to platinum-based chemotherapy among men with metastatic prostate cancer. Cancer. 2017;123:3532-9.
de Bono J, Mateo J, Fizazi K, Saad F, Shore N, Sandhu S, et al. Olaparib for Metastatic Castration-Resistant Prostate Cancer. N Engl J Med. 2020;382:2091-102.
Castella M, Jacquemont C, Thompson EL, Yeo JE, Cheung RS, Huang J-W, et al. FANCI Regulates Recruitment of the FA Core Complex at Sites of DNA Damage Independently of FANCD2. PLOS Genetics. Public Library of Science; 2015;11:e1005563.
Kais Z, Rondinelli B, Holmes A, O'Leary C, Kozono D, D'Andrea AD, et al. FANCD2 Maintains Fork Stability in BRCA1/2-Deficient Tumors and Promotes Alternative End-Joining DNA Repair. Cell Rep. 2016; 15:2488-99.
Behan FM, Iorio F, Picco G, Gonçalves E, Beaver CM, Migliardi G, et al. Prioritization of cancer therapeutic targets using CRISPR-Cas9 screens. Nature. 2019;568:511-6.
Rodriguez-Martin B, Alvarez EG, Baez-Ortega A, Zamora J, Supek F, Demeulemeester J, et al. Pan-cancer analysis of whole genomes identifies driver rearrangements promoted by LINE-1 retrotransposition. Nature Genetics. 2020;1-14.
Pelechano V, Steinmetz LM. Gene regulation by antisense transcription. Nature Reviews Genetics. 2013;14:880-93.
Wood EJ, Chin-Inmanu K, Jia H, Lipovich L. Sense-antisense gene pairs: sequence, transcription, and structure are hot conserved between human and mouse. Front Genet. 2013;4:183.

(Continued)

*Primary Examiner* — Katherine D Salmon
(74) *Attorney, Agent, or Firm* — Brake Hughes Bellermann LLP

(57) ABSTRACT

Disclosed herein is Differential Subclone Eradication and Resistance Analysis (DSER), a method developed to identify molecular targets for improved therapy by direct comparison of genomic features of eradicated and resistant subclones in pre- and post-treatment samples from a patient with BRCA2-deficient metastatic prostate cancer. FANCI and EYA4 were identified as candidate DNA repair-related targets for converting subclones from resistant to eradicable, and RNAi-mediated depletion of FANCI confirmed it as a potential target. The EYA4 alteration was associated with adjacent L1 transposon insertion during cancer evolution upon treatment. L1 activation was inhibited by the antiretroviral drug azidothymidine. In conclusion DSER provides an informative intermediate step toward effective precision cancer medicine, especially in cases with dramatic but temporary metastatic tumor regression. L1 transposon activation may be a modifiable source of cancer genomic heterogeneity, suggesting the potential of leveraging newly discovered triggers and blockers of L1 activity to overcome therapy resistance.

14 Claims, 18 Drawing Sheets
Specification includes a Sequence Listing.

(56) References Cited

OTHER PUBLICATIONS

Wilson IM, Vucic EA, Enfield KSS, Thu KL, Zhang YA, Chari R, et al. EYA4 is inactivated biallelically at a high frequency in sporadic lung cancer and is associated with familial lung cancer risk. Oncogene. 2014;33:4464-73.

Luo M, Li Y, Shi X, Yang W, Zhou F, Sun N, et al. Aberrant methylation of EYA4 promotes epithelial-mesenchymal transition in esophageal squamous cell carcinoma. Cancer Science. 2018;109:1811-24.

Jividen K, Kedzierska KZ, Yang C-S, Szlachta K, Ratan A, Paschal BM. Genomic analysis of DNA repair genes and androgen signaling in prostate cancer. BMC Cancer [Internet]. 2018 [cited May 28, 2021]; 18. Available from: https://www.ncbi.nlm.nih.gov/pmc/articles/PMC6180441/.

Tate JG, Bamford S, Jubb HC, Sondka Z, Beare DM, Bindal N, et al. COSMIC: the Catalogue Of Somatic Mutations In Cancer. Nucleic Acids Res. 2019;47:D941-7.

Schwarz JM, Cooper DN, Schuelke M, Seelow D. MutationTaster2: mutation prediction for the deep-sequencing age. Nature Methods. Nature Publishing Group; 2014;11:361-2.

Choi Y, Sims GE, Murphy S, Miller JR, Chan AP. Predicting the Functional Effect of Amino Acid Substitutions and Indels. PLOS One. Public Library of Science; 2012;7:e46688.

Nguyen HM, Vessella RL, Morrissey C, Brown LG, Coleman IM, Higano CS, et al. LuCaP Prostate Cancer Patient-Derived Xenografts Reflect the Molecular Heterogeneity of Advanced Disease an-d Serve as Models for Evaluating Cancer Therapeutics. Prostate. 2017;77:654-71.

Annala M, Kivinummi K, Tuominen J, Karakurt S, Granberg K, Latonen L, et al. Recurrent SKIL-activating rearrangements in ETS-negative prostate cancer. Oncotarget. 2015;6:6235-50.

Stein-O'Brien G, Kagohara LT, Li S, Thakar M, Ranaweera R, Ozawa H, et al. Integrated time course omics analysis distinguishes immediate therapeutic response from acquired resistance. Genome Med. 2018;10:37.

Jones RB, Garrison KE, Wong JC, Duan EH, Nixon DF, Ostrowski MA. Nucleoside analogue reverse transcriptase inhibitors differentially inhibit human LINE-1 retrotransposition. PLoS One. 2008;3:e1547.

Robinson DR, Wu Y-M, Lonigro RJ, Vats P, Cobain E, Everett J, et al. Integrative clinical genomics of metastatic cancer. Nature. 2017;548:297-303.

Swanton C. Take lessons from cancer evolution to the clinic. Nature. 2020;581:382-3.

Farkash EA, Kao GD, Horman SR, Prak ETL. Gamma radiation increases endonuclease-dependent L1 retrotransposition in a cultured cell assay. Nucleic Acids Res. Oxford Academic; 2006;34:1196-204.

Armando RG, Gómez DLM, Gomez DE. New drugs are not enough-drug repositioning in oncology: An update. Int J Oncol. 2020;56:651-84.

* cited by examiner

METHOD FOR IDENTIFYING TARGETS FOR PRECISION CANCER THERAPY

SEQUENCE LISTING

The text file Sequence_Listing of size 3 KB created Oct. 6, 2021, filed herewith, is hereby incorporated by reference.

TECHNICAL FIELD

This application relates to methods for identifying targets for precision cancer therapy.

BACKGROUND

Understanding the emergence of cancer cell resistance to therapy is central to improving cancer outcomes. A resistant cancer cell subclone is relatively easy to define—it is a population of cancer cells remaining after a patient has received therapy targeting the original cancer cell population. By contrast, a cancer cell subclone eradicated by therapy is relatively hard to define, because it requires reasonable proof that the eradicated subclone no longer exists in the patient after a specific therapy. It is also critical to recognize that key characteristics of an eradicated subclone cannot be imputed solely from characteristics in a resistant subclone, because the point at which characteristics defining resistance arose is not known a priori.

The first cancer subclones genomically proven to be eradicated by specific therapy were reported in 2015 in leukemia (1), where the focus was largely on the emergence of resistance rather than on characteristics of the eradicated subclone. We recently reported a clinically important subclone eradicated by carboplatin chemotherapy in a metastatic prostate cancer (mPC) patient "A34" (2). To our knowledge, this is the first reported genomic evidence of subclone eradication in a solid tumor, a metastatic prostate cancer where we previously reported somatic L1 retrotransposon activity as a source of traceable genomic heterogeneity (3).

The present invention is, at least partly, based on a surprising objective to evaluate whether 1) Prospectively planned, side-by-side Differential Subclone Eradication and Resistance genomic analysis in individual patients with partial responses could provide a uniquely powerful intermediate step for advancing precision cancer medicine, and 2) L1 activation being itself a dynamic source of genomic heterogeneity leading to eradicability or resistance, could this response be blocked by existing medications.

DETAILED DESCRIPTION

Definitions

Figure 1A:
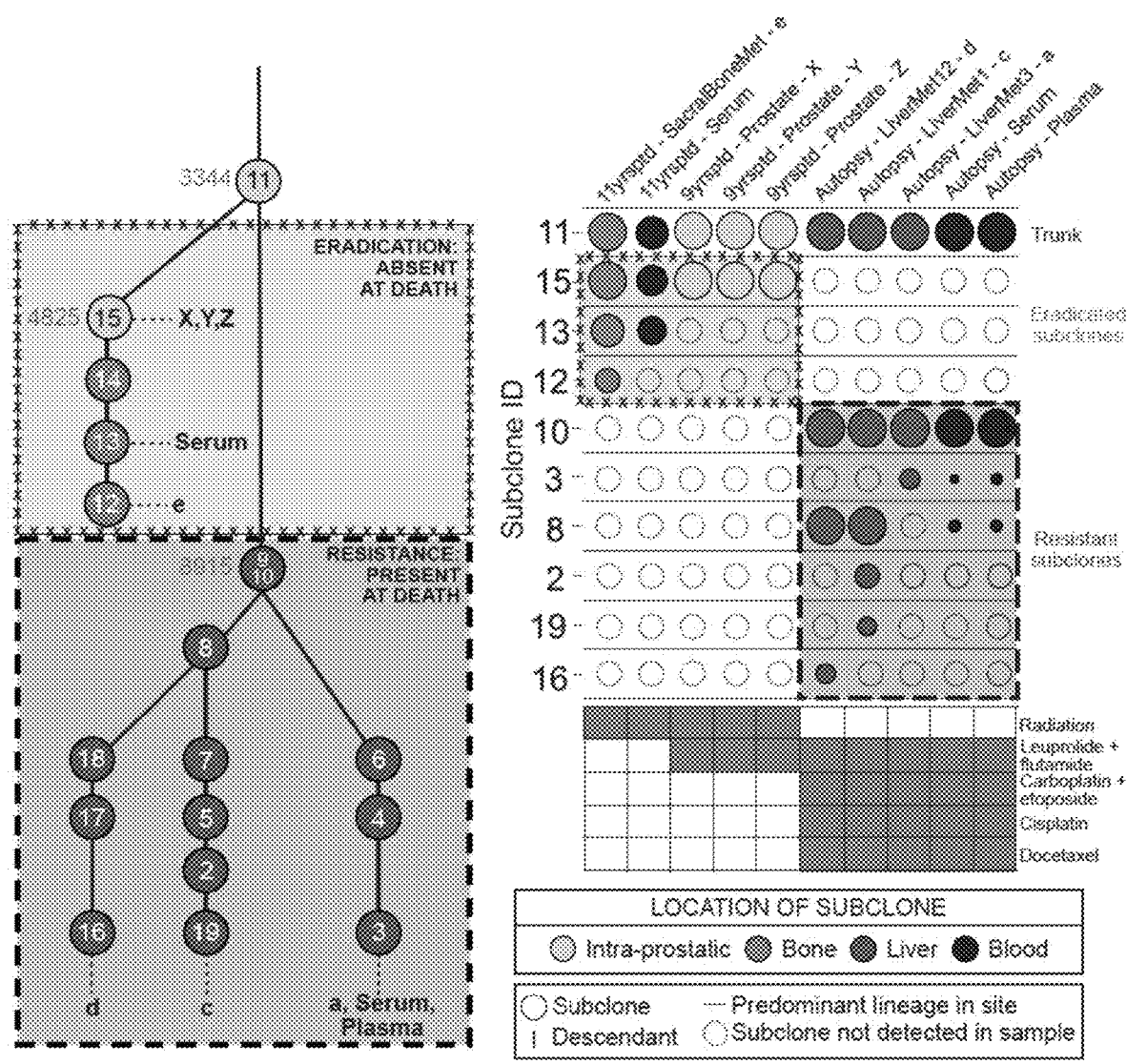
FIG. 1. Genomic evolutionary analysis of primary and metastatic samples and subclones in patient A34 reveals distinct genomic features in resistant and eradicated subclones. (A) Subclonal structure of the lethal metastatic prostate cancer of patient A34, modified from Woodcock et al (2), presented as a phylogenetic tree and subclone and sample button plot. Of the 19 total subclones, 17 were used to construct the phylogenetic tree (2 subclones were excluded as they contained>50% indels). The box composed of black x's encloses numeric identifiers for subclones eradicated by treatment that were not detected in autopsy samples, and box composed of dashed black lines encloses numeric identifiers of subclones found at autopsy that resisted chemotherapy. In the phylogenetic tree, dotted lines connect the final subclone of a lineage with a letter denoting the sample or samples in which it was observed. These letters are associated with sample names listed along the top of the button plot. The gray shade of each subclone in the button plot reflects its anatomic location as shown in the "LOCATION OF SUBCLONE" key. Numbers adjacent to levels of the phylogenetic tree indicate the total number of substitutions present at the indicated point based on WGS data. The button plot also illustrates the subclones detected in each sample, with the area of each circle corresponding to the cancer cell fraction (CCF) of the subclone (CCF of 1 is found in the top (truncal) nodes of the plot). Similar to the phylogenetic tree plot, in the button plot eradicated subclones are enclosed by a box composed of black x's, and detected resistant subclones are surrounded by a box composed of heavy dashed black lines. In the button plot, circles composed of black dashed lines indicate subclones not detected in a sample. Below the button plot, the treatment exposure of samples from patient A34 is shown as a matrix. Eradicated subclones continued to exist after exposure to external beam radiation and androgen deprivation, and therefore subclone eradication is associated with carboplatin plus etoposide chemotherapy. Samples are labeled according to the time of collection (yrsptd=years prior to death) and location. The SacralBoneMet sample is a spinal cord compressing sacral nerve root metastasis removed 11 years prior to the death of the patient. (B) Circos plot tree of L1 insertion events in the whole genome sequencing samples from A34. Curved lines indicate L1 transduction events with determined source elements, with arrowheads indicating the recipient chromosome of each transduction. Black triangles denote solo L1 integration sites (source element unknown). Somatic L1 integration in TARID specific to the eradicated subclone is marked. (C) Barplots of methylation percentage in the CpG island in the promoter region of the EYA4 gene, which may be affected by the L1 insertion into the 3' adjacent sense-antisense paired TARID gene in the SacralBoneMet sample. Solid black bars indicate significantly hypermethylated sites in the SacralBoneMet (black) relative to the same genomic positions in the LiverMet samples and autopsy blood samples (cyan). Violin plots show methylation percentage at the significantly hypermethylated CpG sites in the EYA4 gene promoter, potentially as a consequence of L1 insertion into TARID. (D) Knockdown of FANCI reduces the proliferation of LNCaP but not PC-3 cells. Scrambled (Scr) control siRNA is used as reference. The cell confluence was determined after a 5-day knockdown using IncuCyte S3 Image analysis tools. Asterisks indicate significant difference between sample conditions based on t-test (**, p<0.01).

Unless otherwise defined, the terms and expressions used in this specification and claims have the meanings generally applicable in the field of cancer diagnostics. Some of the terms and expressions used herein are have the meanings defined in the following paragraphs. Further definitions may appear later in the specification.

As used herein, the singular expressions "a", "an" and "the" mean one or more. Thus, a singular noun, unless otherwise specified, carries also the meaning of the corresponding plural noun.

As used herein, the term "cancer" refers to any cancer including, but not limited to, solid tumor cancers such as prostate cancer, stomach cancer, liver cancer, cervix uteri cancer, esophagus, bladder cancer, kidney cancer, pancreatic cancer, squamous cell carcinoma (SCC) such as head and neck squamous cell carcinoma (HNSCC), lung cancer, breast cancer, and colorectal cancer, and hematological cancers such as different types of leukemias, lymphomas and myelomas. Accordingly, it is to be understood that the invention is not limited to any particular cancer type although the experimental part focuses on prostate cancer.

As used herein, the term "cancer cell subclone" and the like refer to a population of cancer cells having a genetic makeup that differs from that of another population of cancer cells in the same patient.

As used herein, the term "resistant cancer cell subclone" and the like refers to a population of cancer cells remaining after a patient has received therapy targeting the original cancer cell population.

As used herein, the term "cancer cell subclone eradicated by therapy" and the like refers to a population of cancer cells that no longer exists in the patient after initial standard cancer therapy.

As used herein, the term "subclonal composition of a sample" and the like refers to the presence of one or more cancer cell subclones in a biological sample.

As used herein, the term "molecular characteristics" of a subclone refers broadly to the molecular makeup of the subclone and includes any multiomic or other molecular data obtainable from the cells of the subclone. Non-limiting examples of such data include any DNA, RNA, protein or other molecular measurement data.

As used herein, the term "sample" refers to a biological sample obtained from a patient whose molecular target for precision cancer therapy is to be identified. Typically, the sample is a sample of a cancerous tissue, be it a primary cancer tissue or a metastatic cancer tissue, or a tissue suspected of being cancerous. The term "sample" also includes samples that have been manipulated or treated in any appropriate way after their procurement including, but not limited to, centrifugation, filtration, precipitation, dialysis, chromatography, treatment with reagents, washing, or enriching for a certain component of the sample such as a cell population.

As used herein, the terms "patient," "individual," and "subject" are used interchangeably, and refer to a mammal, particularly, a human. For veterinary purposes, the terms include mammalian animals such as domestic animals such as livestock, pets and sporting animals. Examples of such animals include without limitation carnivores such as cats and dogs and ungulates such as horses. Also experimental animals such as those used in the development of animal models of disease, including, but not limited to, rodents including mice, rats and hamsters, and primates are included. Accordingly, the present invention may be applied in both human and veterinary medicine.

As used herein, the term "cancer treatment or treatment interval" refers to a specific therapy targeting the original cancer cell population and giving rise to "resistant" and "eradicated" cancer cell subclones. The cancer treatment or treatment interval may comprise, without limitation, chemotherapy, immunotherapy, radiotherapy or any combination thereof. In this context, "cancer treatment or treatment interval" is to be distinguished from later precision cancer therapy directed to a molecular target identified in accordance with the present invention and directed specifically to the cancer cell subclone resistant to the prior cancer treatment or treatment interval.

As used herein, the term "precision cancer therapy" refers to enhanced cancer therapy targeting the resistant cancer cell subclone remaining after the prior cancer treatment or treatment modality. More specifically, the precision cancer therapy is directed to a molecular target identified by the method of the invention. In an embodiment, the precision cancer therapy is patient-specific.

As used herein, the term "molecular target" refers broadly to any molecular entity including, but not limited to, a DNA region such as a gene, a regulatory element thereof or a non-coding region, RNA, a protein, or any other cellular compound such as a lipid that is differentially expressed in eradicated and resistant cancer cell subclones. Alternatively, the molecular target may comprise a mutation either in the eradicated or in the resistant cancer cells.

As used herein, the term "increased expression" refers to an increase in the amount of a target mRNA or protein in a resistant subclone of cancer cells as compared with an eradicated subclone of cancer cells. Said increase may be determined on the basis of qualitative and/or quantitative assessment using standard methods known in the art. The expression is increased if the amount or level of the target mRNA or protein in the resistant subclone is, for instance, at least about 1.5 times, 1.75 times, 2 times, 3 times, 4 times, 5 times, 6 times, 8 times, 9 times, time times, 10 times, 20 times or 30 times the amount of the mRNA or protein in the eradicated subclone. Preferably, the term "increased expression" refers to a statistically significant increase in the level of expression.

As used herein, the term "decreased expression" refers to a decrease in the amount of a target mRNA or protein in a resistant subclone of cancer cells as compared with an eradicated subclone of cancer cells. Said decrease can be determined qualitatively and/or quantitatively according to standard methods known in the art. The expression is decreased if the amount or level of the target mRNA or protein in the resistant subclone is, for instance, at least about 1.5 times, 1.75 times, 2 times, 3 times, 4 times, 5 times, 6 times, 8 times, 9 times, time times, 10 times, 20 times or 30 times lower than the amount of the mRNA or protein in the eradicated subclone. Preferably, the term "decreased expression" refers to a statistically significant decrease in the level of expression.

As used herein, the terms "treatment" and "treating", and the like, refer to the administration of cancer therapeutics to a patient in need thereof for purposes which may include ameliorating, lessening, inhibiting, or curing cancer. Amounts and regimens for the administration of said therapeutics may be determined readily by those with ordinary skill in the clinical art of cancer therapy. Generally, the dosage of the therapeutics will vary depending on considerations such as: age, gender and general health of the patient to be treated; kind of concurrent treatment, if any; frequency of treatment and nature of the effect desired; duration of the symptoms; and other variables to be adjusted by the individual physician. A desired dose can be administered in one or more applications to obtain the desired results, using any appropriate route of administration. In addition, therapeutics may be used alone or in combination i.e. administered simultaneously, separately or sequentially with other pharmaceutical drugs or treatment modalities.

As used herein, the term "effective amount" refers to an amount of cancer therapeutics by which harmful effects of cancer are, at a minimum, ameliorated.

It is to be understood that this invention is not limited to any particular methodology, protocols, reagents, and formulations described, as such may vary. It is also to be understood that the terminology used herein is for the purpose of describing particular embodiments only and is not intended to limit the scope of the present invention, which will be limited only by the appended claims.

METHODS OF INVENTION

The invention relates to differential analysis of eradicated and resistant cancer cell subclones as a novel approach to identify targetable alterations and resistance mechanisms. Herein, this approach is referred to as Differential Subclone Eradication and Resistance Analysis (DSER), In essence, DSER is based on comparing samples obtained from a patient before and after subclone eradication. Basically any multiomic data, including, but not limited to, DNA, RNA, protein, or other molecular measurement data can be used and combined in the comparison.

In some embodiments, the differential analysis may be based on comparison of any available sequence data such as whole genome sequencing (WGS) data or deep targeted sequence data, CpG methylation data (increased promoter region methylation may at least in some instances indicate lower levels of protein expression), and/or mRNA or protein expression data.

Being based on comparison of patient samples before and after subclone eradication, DSER is a tool to identify patient-specific targets for precision cancer therapy.

Typically, obtaining the patient samples is not part of DSER. Consequently, DSER may be regarded as an in vitro method carried out on patient samples obtained earlier.

In some embodiments, the differential analysis may focus on genes or proteins associated with DNA repair pathways. By way of illustration, the experimental part demonstrates how FANCD2/FANCI and EYA4 were identified as potential DNA repair-related target genes for precision cancer therapy by the present differential analysis of eradicated and resistant cancer cell subclones. Accordingly, an aspect of the invention concerns a method of treating cancer in a patient in need thereof, the method comprising administering an agent that silences or inhibits the expression of FANCD2/FANCI or EYA4. This aspect may also be formulated as a therapeutic use of an agent that silences or inhibits the expression of FANCD2/FANCI or EYA4 for the treatment of cancer. Means and method for silencing or inhibiting FANCD2/FANCI or EYA4 are available to those skilled in the art.

The purpose of the differential analysis is to identify differences contributing to resistance and thus targets for precision cancer therapy.

Once a molecular target has been identified, it may be targeted by any appropriate means and methods available in the art. Accordingly, the disclosed method of identifying a target for precision cancer therapy in patient in need thereof may, in some embodiments, comprise administering appropriate targeted therapeutics to said patient. This aspect of the invention may also be formulated as a method of treating cancer in a patient in need thereof, wherein the method comprises first identifying a molecular target for precision cancer therapy in accordance with what is disclosed herein, and then applying said precision cancer therapy to the patient.

In some embodiments, the present method of identifying a molecular target for precision cancer therapy does not comprise any therapeutic treatment steps.

If the expression of the target gene is upregulated in a resistant subclone of cancer cells as compared to an eradicated subclone, targeted therapeutics to be applied may in some embodiments aim at decreasing or inhibiting the expression of the target gene or blocking the function of a protein encoded by the target gene. This end may be achieved by employing various techniques as well known in the art. For example, loss of a certain protein or a loss of a certain transcript may be achieved by antisense therapy or RNA interference (RNAi). The most common approach for RNAi-based gene silencing is the use of small interfering RNA (siRNA). Non-limiting examples of alternative approaches for RNAi include the use of short-hairpin RNAs (shRNAs), Dicer substrate siRNAs (DsiRNAs), and artificial microRNA (miRNA) precursors. Those skilled in the art understand how to apply these approaches for targeted cancer therapy.

Delivery of target-specific RNAi molecules can be accomplished in two principally different ways: 1) endogenous transcription of a polynucleotide encoding the RNAi molecule, or 2) exogenous delivery of the RNAi molecule. For endogenous transcription, target-specific RNAi molecules may be inserted into suitable expression systems using methods known in the art. Non-limiting examples of such expression systems include retroviral vectors, adenoviral vectors, lentiviral vectors, other viral vectors, expression cassettes, and plasmids, such as those encapsulated in pegylated immunoliposomes (PILs), with or without one or more inducible promoters known in the art. For exogenous delivery, RNAi molecules are typically complexed with liposome or lipid-based carriers, cholesterol conjugates, or polyethyleneimine (PEI).

In some embodiments, targeted cancer therapeutics may involve blocking of the function of a target protein. This end may be achieved, for example, through the use of blocking peptides, antibodies, antigen binding antibody fragments or single chain variants thereof, nanobodies, affibodies or aptamers. Those skilled in the art understand how to design and prepare appropriate targeting agents for any given molecular target and how to apply these approaches for targeted cancer therapy.

If resistance to the initial standard therapy is due to a mutated gene causing a necessary protein to be faulty or missing, gene therapy may be applied to introduce a normal copy of the gene to restore the function of the protein. This may be achieved by replacing a defective gene using any available gene editing technique such as a CRISPR-Cas system as well known in the art, or by supplementing a gene product that is not produced in a therapeutically effective amount or at a therapeutically useful time by introducing an appropriate polynucleotide encoding the target protein as desired, for example, as naked DNA by electroporation, gene bombardment, sonoporation, magnetofection, lipofection, or liposome-mediated nucleic acid delivery, or with the aid of vectors such as viral vectors, including but not limited to retroviral vectors, such as lentivirus vectors, adeno-associated viral vectors, and adenoviral vectors.

It is also envisaged that a molecular target identified by DSER in a remaining resistant subclone can be used to engineer a delivery vehicle, such as a virus or bacteria, that will home to the cells of the resistant subclone through a target-specific element comprised in the vehicle and deliver its payload such as RNA, DNA, a protein produced by the bacteria or virus or a drug, without limitation, to the resistant cancer cells.

Furthermore, it is disclosed herein that L1 activity associated with resistance is induced by current cancer therapies and blocked by azidothymidine. Thus, an aspect of the invention relates to azidothymidine and functionally equivalent selective reverse transcriptase inhibitors as cancer therapeutics to prevent L1 activity. This aspect of the invention may also be formulated as a method of preventing L1 activity in a cancer patient in need thereof, comprising administering azidothymidine or a functional equivalent thereof to the patient.

It is to be understood that any one or more of the features of the herein-described embodiments can be combined in any manner with one or more features of any other embodiments in the present specification. Moreover, the following experimental examples are offered by way of illustration, not by way of limitation.

EXPERIMENTAL PART

Figure 4:
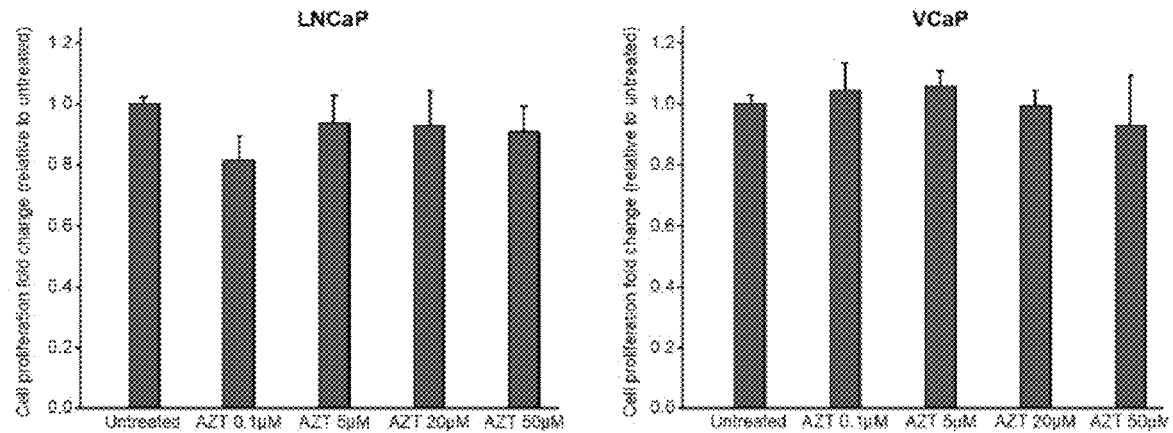
FIG. 4. AZT treatment of LNCaP and VCaP cell lines. As a preliminary study, we explored whether AZT has any cytotoxic effect in LNCaP or VCaP cells. The cells were exposed to various concentrations of AZT (0.1, 5, 20, 50 uM) for 5 days and cell confluence was determined using IncuCyte S3. The effect of AZT on cell proliferation was calculated relative to the untreated control. No significant cytotoxic effect was seen up to 50 uM AZT treatment.

Methods
A34 Samples and DNA Data
Tissue and blood samples from patient A34 were collected as part of the PELICAN integrated clinical-molecular autopsy study of lethal prostate cancer (Table 1). The patient gave informed written consent to participate in the John Hopkins Medicine IRB-approved study. Detailed specimen isolation and analysis methods are contained in Woodcock et al (2).
Identification of L1 Insertion Sites
Whole genome sequencing reads aligned to hg19 from A34 metastatic samples were analyzed for somatic L1 insertions (solo-L1 insertions or L1-mediated transductions) using TraFiC-mem v1.1 (3).
Generation and Analysis of CpG Methylation Data
From A34 metastatic and autopsy blood DNA samples, paired-end reads generated from Illumina TruSeq Methyl Capture EPIC libraries were quality controlled, trimmed and aligned to hg19 genome using Bismark v0.22.3 and Bowtie v2.3.4.1. MethylKit v1.11.0 was used for differential methylation analysis.
Cell Culture
LNCaP and 22Rv1 cells were cultured in a humidified $CO_2$-incubator at 37° C. in Gibco™ RPMI 1640 (1×) media (Thermo Fisher Scientific) supplemented with 10% FBS (Gibco standard FBS, Thermo Fisher Scientific), 2 mM L-Glutamine (Gibco®, Thermo Fisher Scientific), and combination of 100 U/ml Penicillin and 100 µg/mL Streptomycin (Gibco® Pen Strep, Thermo Fisher Scientific). For VCaP cells, Dulbecco's Modified Eagle Medium (DMEM, Gibco, Thermo Fisher Scientific) supplemented with 10% FBS (GE Healthcare™ HyClone™) and for PC-3 F-12 K medium supplemented with 10% FBS, and antibiotics as for LNCaP growth medium was used. Cell lines were obtained from ATCC, authenticated using STR (Short Tandem Repeat) markers and *Mycoplasma*-tested.
Exposure of Cell Lines to Carboplatin/Enzalutamide Alone
Carboplatin or enzalutamide dissolved in DMSO and culture medium without FBS was added after a 24-hour initial incubation period. To control cells DMSO diluted in culture medium was added to a final concentration of 0.02%. LNCaP prostate cancer cells were transfected with L1 plasmid or positive and negative control plasmids and treated with carboplatin (5 µM) or ENZ (10 µM) the day after transfection, and cells were monitored for five days.
Exposure of Cell Lines to Carboplatin/Enzalutamide and AZT
First, the potential cell toxicity of AZT alone was determined and no effects of AZT on cell viability were seen up to 50 µM tested in LNCaP or VCaP cells (FIG. 4). Next, AZT was introduced to both LNCaP and VCaP cells alone and in combination with carboplatin or ENZ.
L1-EGFP Retrotransposition Assay
The setup of the retrotransposition assay and the creation of the plasmids containing an L1RP (4) element tagged with Green Fluorescent Protein (GFP) were as described by Ostertag et al. (5) and implemented as shown in Faulkner et al (6) with some modifications.
siRNA Silencing
LNCaP or PC-3 cells were reverse transfected with 25 nM siRNAs against FANCI (Dharmacon, ON-TARGETplus SMARTpool, L-022320-01-0005; target sequences SEQ ID NOs 9 to 12) or Scr control (Dharmacon, non-targeting pool; target sequences SEQ ID NOs 13 to 16), using OPTI-MEM and Lipofectamine 2000 transfection reagent (Invitrogen) in three biological replicates on 12-well plates. Samples were collected after 72 hours for mRNA isolation.

Cell Proliferation Assay

For cell proliferation assays, cells were reverse transfected with 25 nM siRNAs against FANCI (Dharmacon, ON-TARGETplus SMARTpool, L-022320-01-0005) or Scr control (Dharmacon, non-targeting pool), using OPTI-MEM and Lipofectamine 2000 transfection reagent (Invitrogen) in four biological replicates in a 384-well plate. LNCaP cells were plated on the wells (1000 cells/well) in antibiotic free regular growth medium. After 48 h, vehicle control (DMSO) or Carboplatin dilutions were added into wells in appropriate concentrations diluted in FBS free medium and the cell confluence was monitored for five days using live-cell imaging (IncuCyte S3, Sartorius). Cell confluence was determined by automatic counting using IncuCyte S3 Image analysis tools. Cell confluence (confluence mask) on each time point was calculated based on phase-contrast imaging with a minimum area filter of 150 μm2, segmentation adjustment of 1.0, 100 μm2 cleanup and size adjust of −2 pixels. Confluence curves were compared for statistical differences between treatment conditions at each timepoint using t-test.

Quantitative Real-Time PCR

The isolation of RNA from cell lines was conducted using TriPure Isolation Reagent (Roche) following the manufacturer's protocol. The concentration of the RNA samples was measured using NanoDrop™ One/OneC Microvolume UV-Vis Spectrophotometer, followed by dilution of the samples to 1 μg/μl. The conversion of 1 μg of RNA to cDNA was done using Transcriptor First Strand cDNA Synthesis Kit (Roche) according to the manufacturer's instructions. The RT-PCR run was performed using LightCycler™ 480 SYBR Green I Master (Roche) and The LightCycler® 480 Real-Time PCR System (Roche) with 96-multiwell format. To allow separate analysis of ORF1 and ORF2, two sets of primer pairs were designed to target the L1RP-ORF1 (ORF1 mRNA thereafter), L1RP-ORF2 (ORF2 mRNA thereafter) and FANCI (Table 2). Each run included two biological and two technical replicates per treatment with fold change calculated based on the obtained Ct-values. Normalization was done against GAPDH values measured (Table 2).

Western Blot

Whole cell lysates were prepared using SDS sample buffer (66 mM Tris-HCl pH 6.8, 13% Glyserol, 2.1% SDS and 0.01% Bromophenol Blue) with protease inhibitor added (cOmplete™ Protease Inhibitor Cocktail, Roche).

Estimation of L1 mRNA Levels from RNA-Seq

RNA sequencing reads were quality controlled (TrimGalore v0.6.5), trimmed (Cutadapt v1.18), and aligned to the hg38 genome (STAR v2.7.8 with Gencode Release 33 annotations). featureCounts v2.0.2 (7) was used to quantify reads within 146 putatively retrotransposition-active human L1 elements with intact ORF1 and ORF2 as annotated in the L1Base2 database. Counts were normalized in each sample to represent the number of reads mapping to the putatively active L1 elements per million aligned reads in the sample.

Results

Distinct Eradicated and Resistant Subclones

Figure 5:
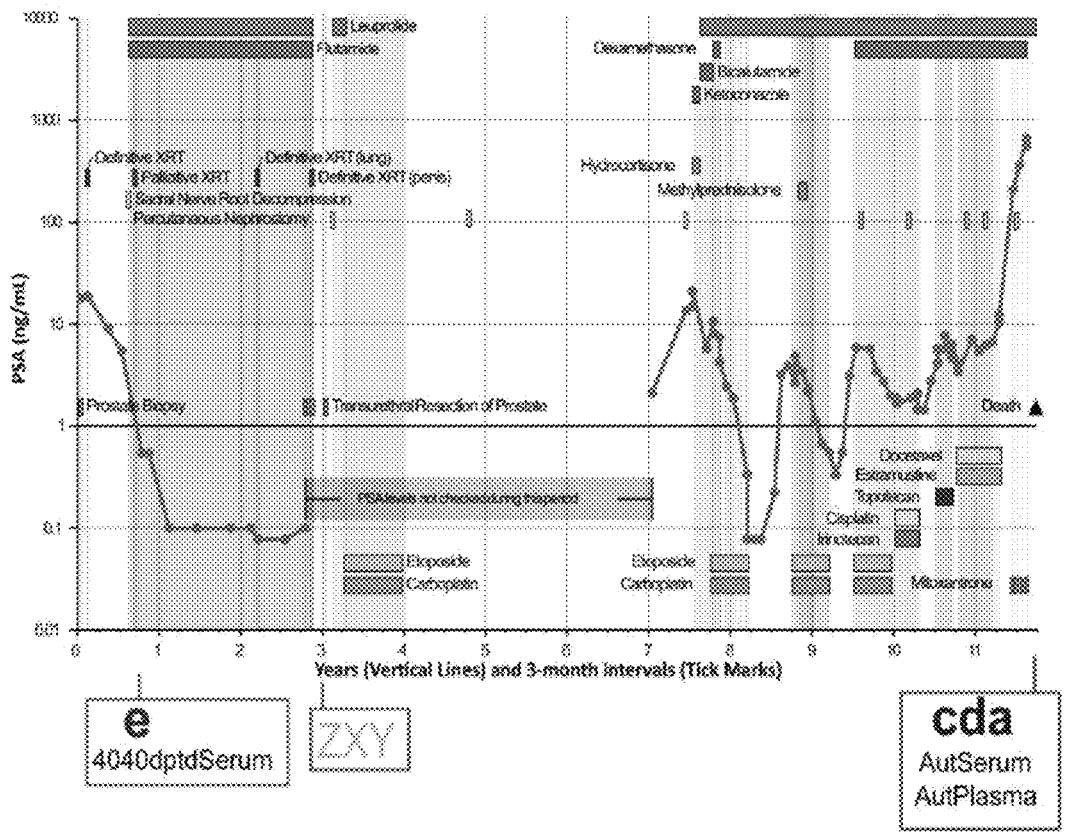
FIG. 5. A34 clinical timeline and samples analyzed. At age 54 (age changed between −3 and 3 years according to study consent) patient A34 developed a single episode of painless hematuria, triggering a visit to his physician. On digital rectal exam he was found to have an indurated right lobe of the prostate. Prostate biopsy showed Gleason score 2+3=5 prostate adenocarcinoma. Serum PSA at diagnosis was 16.2 ng/mL and technetium (99mTc MDP) bone scan and prostate acid phosphatase were normal. He then received 6400 cGy external beam radiation to his prostate with intent to cure. Seven months later he developed leg pain and perineal numbness, and underwent S1-S3 decompressive laminectomy, when a sample of the metastatic tumor tissue ("e") and serum sample (used for cell-free circulating DNA isolation) were obtained. A34 commenced leuprolide/flutamide androgen deprivation at the time of laminectomy, and received 4500 cGy palliative radiation to the sacrum starting 1 month after laminectomy. A routine chest radiogram 18 months after laminectomy revealed a left hilar mass, bronchoscopic biopsy showed poorly differentiated carcinoma with glandular features, and he received 6000 cGy radiation to the left lung hilum. Eight months later he was found to have a prostate cancer penile skin metastasis confirmed by biopsy. He also underwent transurethral resection of the prostate for urinary obstructive symptoms at the same time when prostate carcinoma tissue Z, X, and Y were obtained as shown. He subsequently received 4000 cGy radiation to the penis. Bilateral percutaneous nephrostomy tubes were placed when urinary obstruction symptoms persisted. Six months later he received a first course of Carboplatin and Etoposide chemotherapy. The patient felt dramatically better after chemotherapy, and refused to see doctors except for nephrostomy tube change for the ensuing three years. He then presented with severe lethargy, and over the ensuing four years underwent three additional courses of carboplatin/etoposide and other chemotherapy as shown. Peak serum PSA close to death was 603.1 ng/mL. At autopsy, large liver metastases nearly consumed the liver, and metastases to lumbosacral bone and perirenal area were present. No lung metastases were present. Metastatic cancer DNA and RNA samples from three separate liver metastases ("cda"), and cell-free circulating DNA were obtained at autopsy for the analysis.

Patient A34 presented with 19 distinct subclones across his primary tumor and metastases that could be identified via analysis of DNA single-nucleotide variants (SNVs) and indels using the DPClust method as previously shown (2). Four cancer subclones specific to the sacral bone metastasis removed at surgery 11 years prior to death were also present in serum and transurethral resection of the prostate cancer samples prior to carboplatin chemotherapy, but absent from three liver metastases and serum and plasma sampled at autopsy, consistent with eradication by carboplatin chemotherapy (FIG. 1A, FIG. 5) (2). Neither androgen deprivation therapy nor radiation therapy were the cause of this subclone eradication because one of the eradicated subclones is still detected in samples Z, X, and Y that were obtained by transurethral resection from the prostate after androgen deprivation and after radiation therapy to the prostate, sacrum, lung, and penis (FIG. 1A, FIG. 5). Resistant subclones (but not eradicated subclones) were detected in the liver metastases and autopsy blood samples, with subclone detection in autopsy serum and plasma consistent with separate shedding of tumor DNA into blood by distinct liver metastases. Based on these findings, if eradicated subclones were still present in A34's body at the time of death, there is a reasonable expectation that they would have shed tumor DNA detectable by the deep targeted sequencing performed, and no such signals were detected (FIG. 1A).

Genomic Lesions Potentially Conferring Eradicability

We analyzed A34 WGS and deep targeted sequence data previously reported (2, 8), and supplemented this with genome-wide CpG methylation data to investigate the potential causes of selective cancer subclone eradication and resistance. Despite the presence of 4825 total substitutions in the eradicated subclones, with identified truncal drivers including biallelic inactivation of BRCA2, PTEN LOH, mutations in CEBPA and ARID1A and subclonal FOXA1 amplification, subclones 15, 14, 13, and 12 were eradicated by carboplatin and etoposide chemotherapy (FIG. 1A, FIG. 5) (2, 8).

Figure 6:
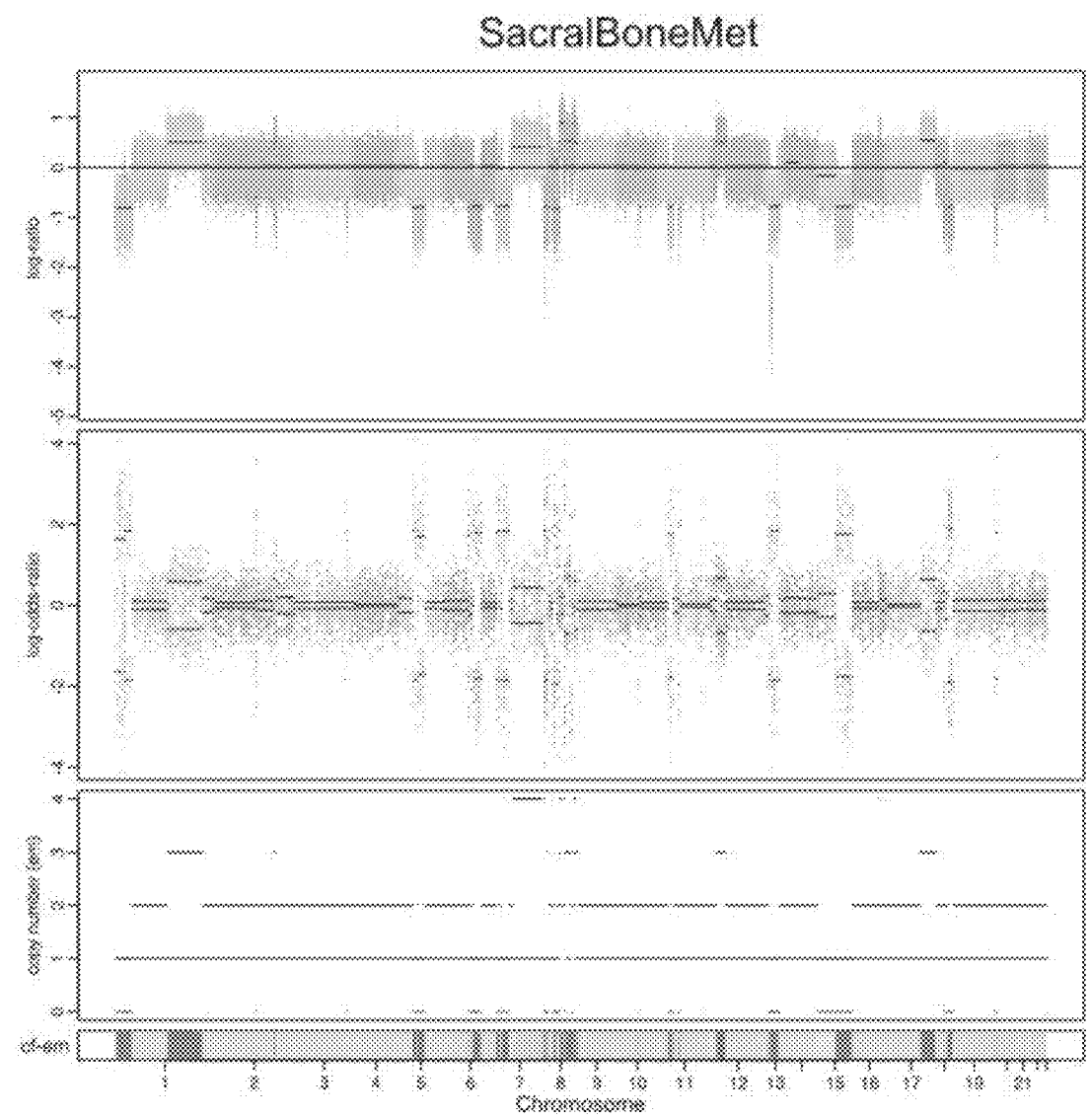
FIG. 6. Allele-specific copy number profiles of A34 metastatic samples. A figure is included for each sample, with chromosomes shown as alternating light gray and darker gray. Mean values for segments are shown as horizontal black lines. The top panel of each figure shows the log-ratio of read depth in the metastatic sample compared to the normal sample. The second panel shows the log-odds ratio of variant allele counts in the metastatic sample compared to the normal sample. The third panel shows total and minor copy number as two parallel black lines. The chromosome bar at the bottom of each figure depicts estimated cellular fraction (cf), where the dark gray color indicates high cellular fraction, light gray indicates low cellular fraction, and medium gray indicates a diploid segment where total copy number is 2 and minor copy number is 1 (4).
Figure 6:
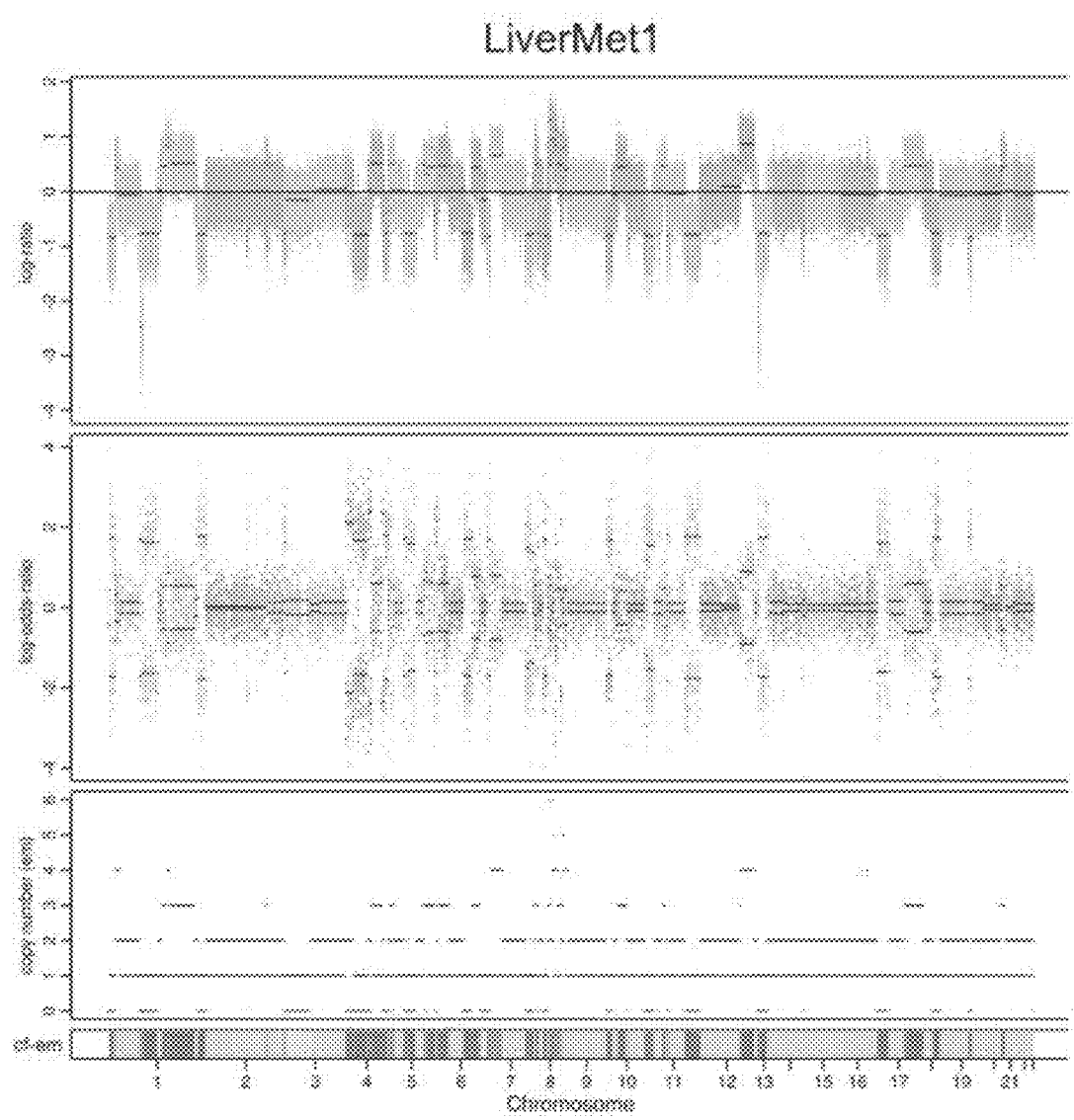
Figure 6:
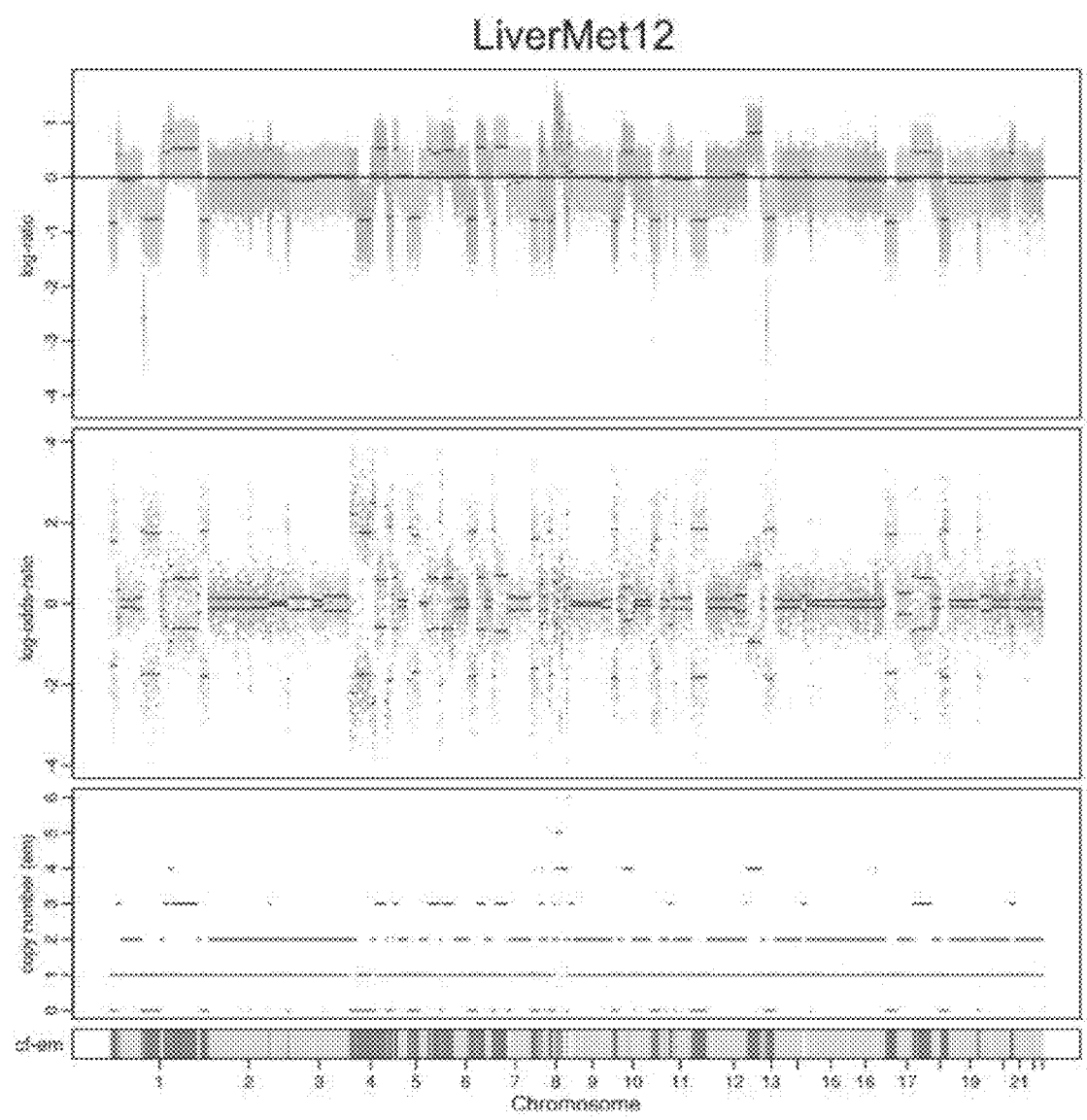
Figure 6:
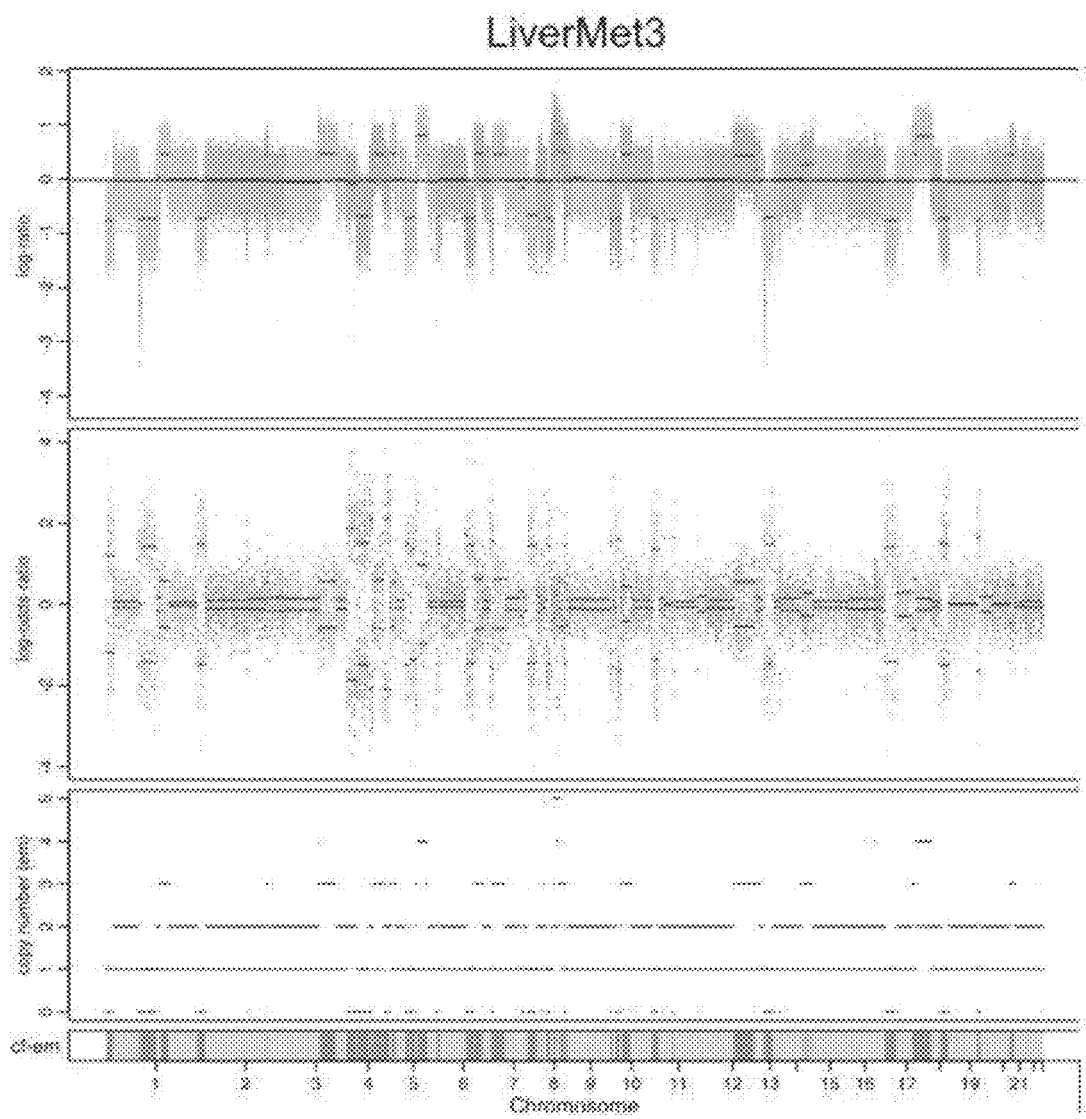
Figure 7A:
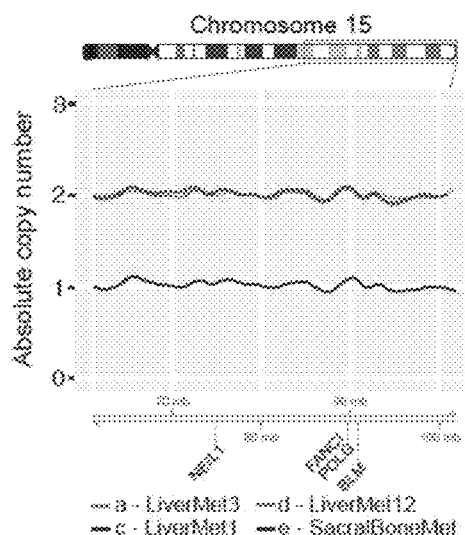
FIG. 7. Additional data supporting FANCI as target identified by DSER analysis. (A) Line plots of absolute copy number showing one copy loss of a ~40 Mbp region of chromosome 15 specific to the SacralBoneMet sample harboring the eradicated subclones in A34. We confirmed the absence of 15q copy neutral loss-of-heterozygosity in the LiverMet samples FIG. 6). The lost region of 15q contains 295 protein-coding genes, of which four are DNA repair-implicated: NEILL FANCI, POLG, and BLM. These genes are marked along the genomic axis at the bottom of the plot. (B) PICKLES database essentiality scores based on data from Behan et al (53) for the four DNA repair-related genes (FANCI, POLG, BLM, and NEILI) located in the chr15q region with loss of heterozygosity in the sacral bone metastasis sample. FANCI has a positive essentiality score in 22Rv1 and LNCaP cells, suggesting it may be necessary for cell survival. The essentiality score is a quantile normalized Bayes factor that represents the level of confidence that the gene is essential. (C) Barplots confirming FANCI siRNA knockdown in PC-3 and LNCaP cells based on significantly reduced FANCI mRNA expression level compared to scrambled (Scr). mRNA expression values were normalized against measured GAPDH expression values. (D) LNCaP cell confluency curves when exposed to FANCI siRNA and varying concentrations of carboplatin. Scrambled (Scr) siRNA is shown as a control. t-test was used to determine statistical significance of sample conditions at each timepoint compared to FANCI siRNA (left) and Scr (middle and right) (*, $p<0.05$; , $p<0.01$; *, $p<0.001$).
Figure 7B:
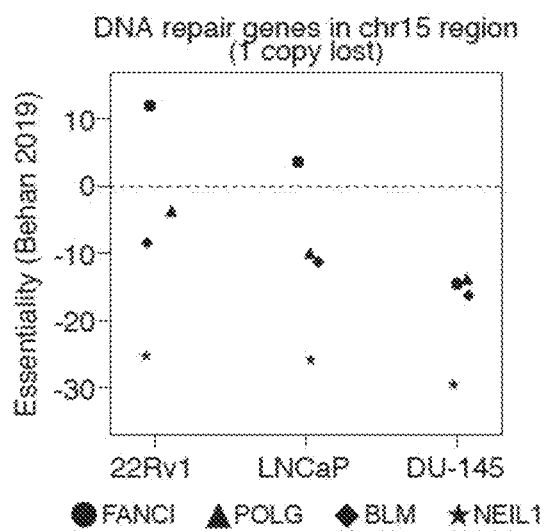

Since BRCA2-deficient tumors have recently been proven responsive to chemotherapy leveraging their decreased DNA-repair capacity (9, 10), we hypothesized that the eradicated subclones may have had additional genomic lesions conferring increased sensitivity to DNA damage. We searched for alterations in currently known members of DNA repair pathways. The chemotherapy-eradicated subclone harbored a 40 Mbp heterozygous deletion in the q-arm of chromosome 15 that contains 295 protein-coding genes, four of which have functions involving DNA repair (NEIL 1, FANCI, POLG, and BLM) (FIG. 6, FIG. 7A). Of these, FANCI is of particular interest as it belongs to the same Fanconi Anemia gene family as BRCA2, regulates recruitment of the Fanconi Anemia core complex at sites of DNA damage independent of FANCD2 (11), and has been previously shown to reduce BRCA1/2-deficient cell survival when depleted in an ovarian cancer model (12). Additionally, FANCI is the only DNA repair gene within the region deemed essential for prostate cancer cells in CRISPR knock-out experiments from the PICKLES database (FIG. 7B) (13).

Figure 1B:
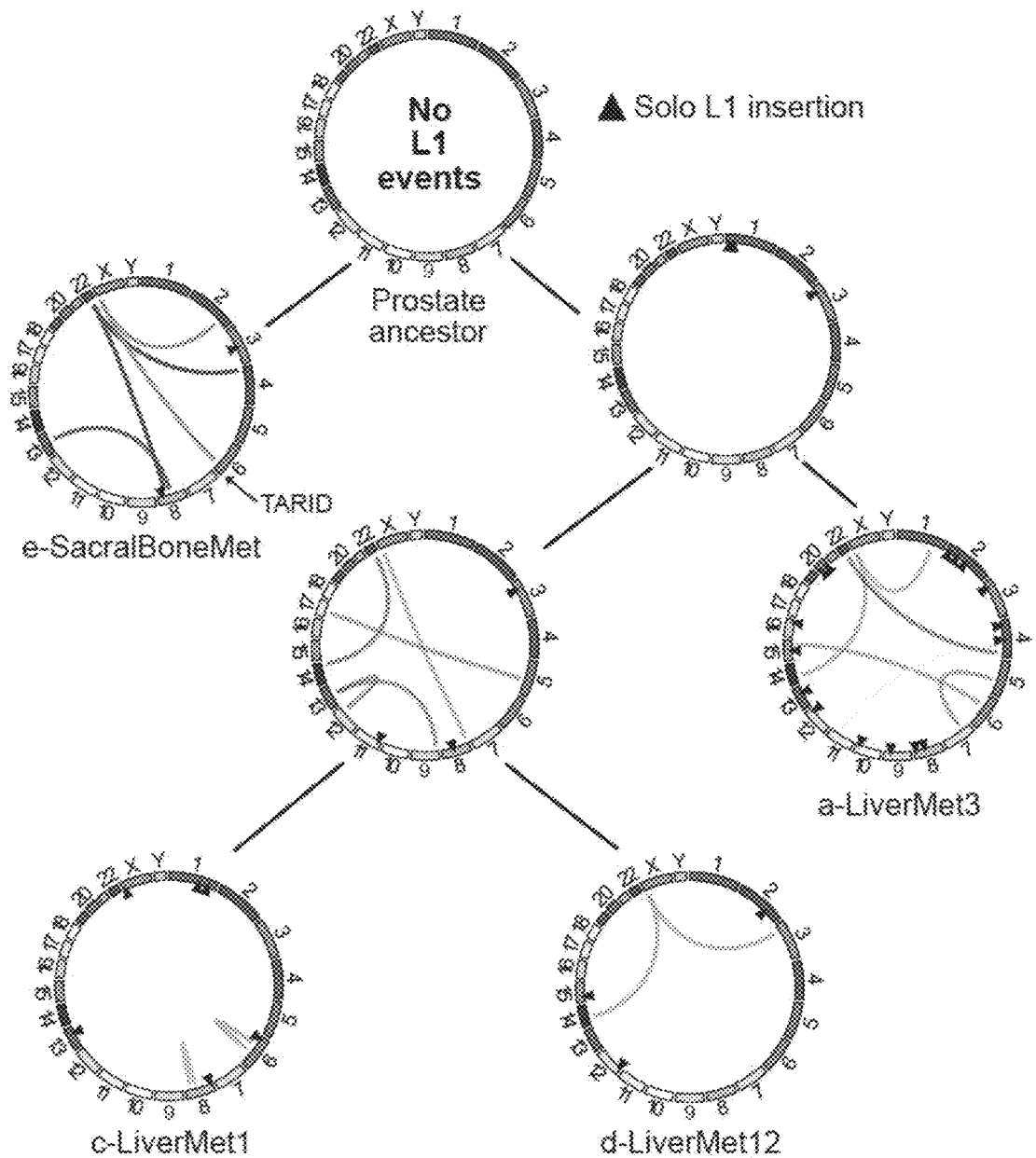

Extending the analysis to somatic L1 transposon transduction during the evolution of metastases in A34, we used updated L1 detection algorithms to extend the resolution of these findings, identifying a total of 50 L1 insertion events across A34 cancer DNA samples (FIG. 1B). Notably, we observed repeated unique transductions from the same source elements on chrXp22.2, chr22q12.1, chr13q21.2, and chr5q21.3 across the L1 somatic evolutionary tree (FIG. 1B). All of these elements have recently been shown to be recurrent sources of L1 transductions in multiple cancer types, including prostate, with the elements on chrXp22.2 and chr22q12.1 being particularly frequent sources of transductions (14).

Figure 1C:
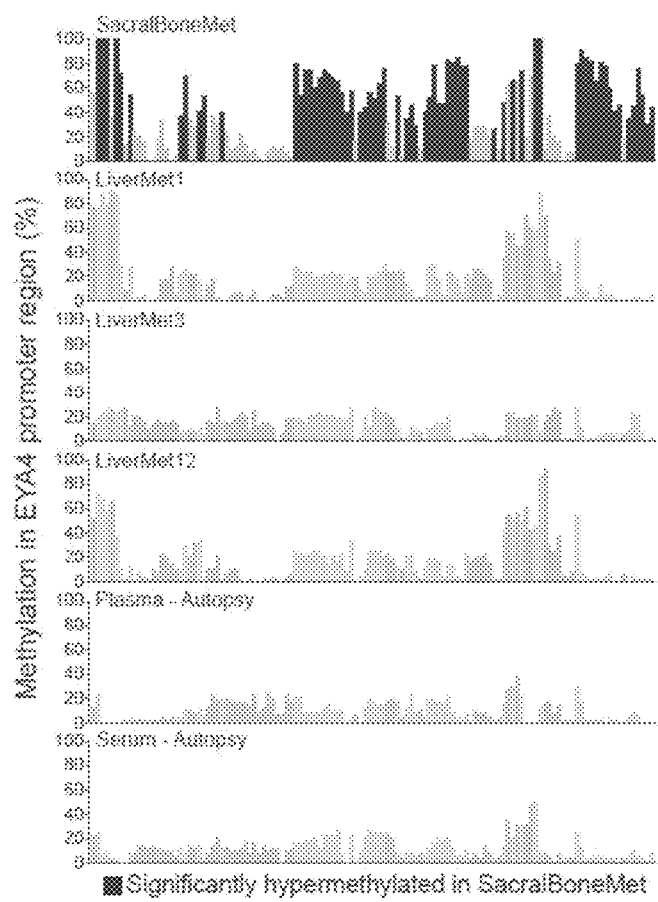
Figure 1C:
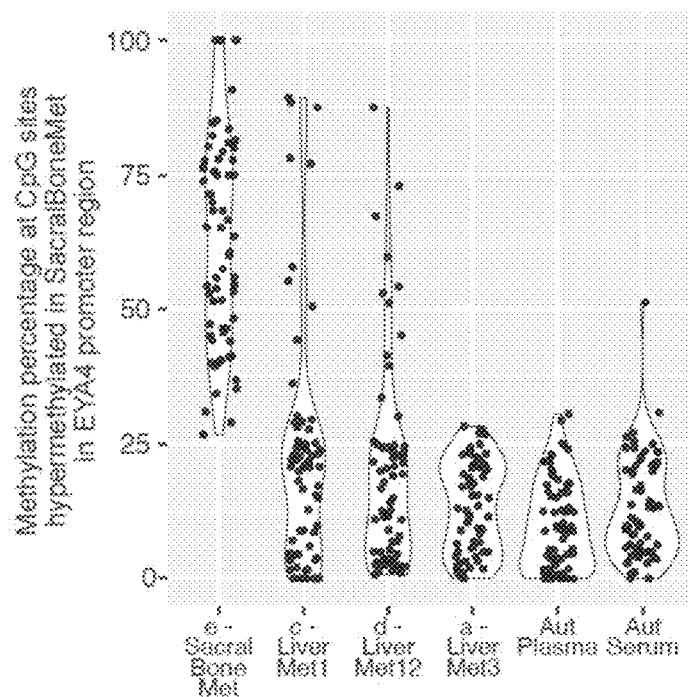

The eradicated sacral bone metastasis subclone harbored a unique profile of 7 L1 insertions not found in the resistant subclones, one of which was a 595 bp L1 transduction from the chromosome Xp22.2 source element into the TARID gene intron 3 (FIG. 1B). TARID functions as a promoter demethylase and forms a sense-antisense gene pair with the gene EYA4, suggesting that TARID may have a role in EYA4 transcriptional regulation (15, 16). Accordingly, we found the EYA4 promoter significantly hypermethylated in the eradicated sacral bone metastasis compared to the resistant liver metastases and autopsy blood samples (66/122 (54%) CpG sites) (FIG. 1C). Transcriptome analysis of the sacral bone metastasis was not possible because no remaining tissue material is available, but the increased methylation of the EYA4 promoter region nonetheless points to possible lower levels of expression of EYA4. Previous studies have found cells with an absence of EYA4 expression to be more sensitive to DNA damage upon exposure to cisplatin (17, 18).

Figure 1D:
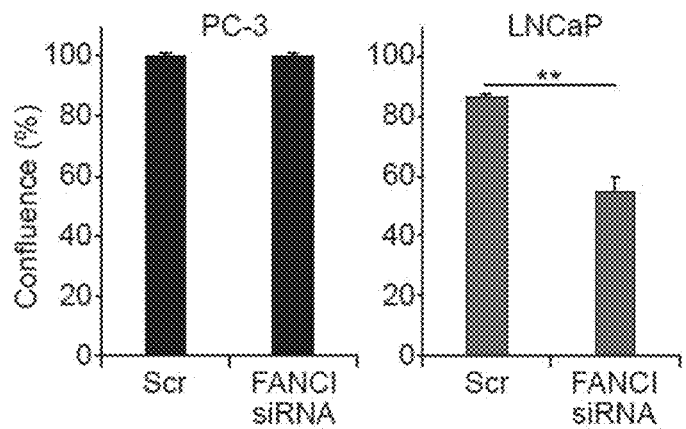
Figure 7C:
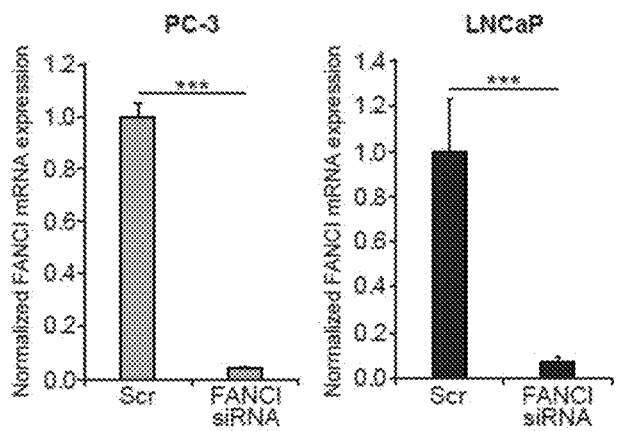
Figure 7D:
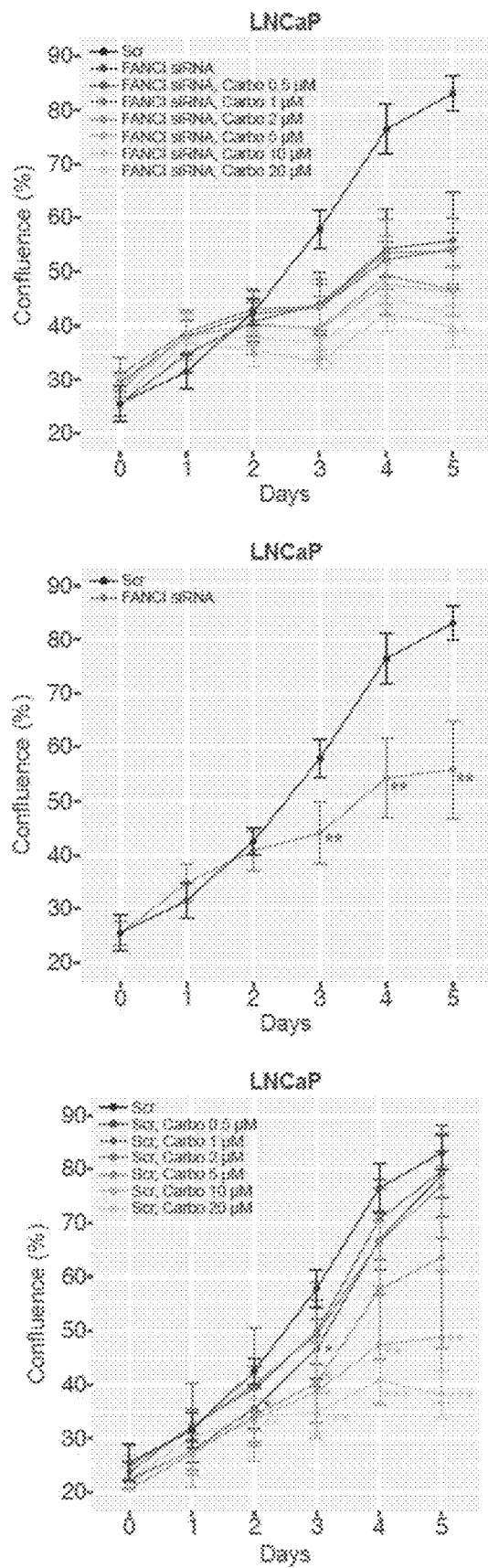

As a test of the hypothesis that decreased FANCI function could have contributed to selective subclone eradication, we exposed prostate cancer cell lines PC-3 and LNCaP to FANCI siRNA with and without carboplatin treatment. The inhibition of FANCI resulted in a significant decrease in the proliferation of LNCaP cells while no effect was observed in PC-3 cells (FIG. 1D, FIG. 7C-D), confirming FANCI's role in maintaining LNCaP capacity to undergo cell division. Exposure of siFANCI LNCaP cells to 10 μM carboplatin additionally significantly decreased proliferation (FIG. 7D). Similar to BRCA2 somatic inactivation in A34, LNCaP (but not PC-3) contains deficient RAD50 and CHEK2 functions upstream of the BRCA complex, again supporting increased dependency on FANCI in BRCA-deficient tumors (19).

Genomic Lesions Potentially Conferring Gradual Increase in Resistance to Chemotherapy in Resistant Subclones The resistant subclones identified in liver metastases, serum, and plasma contained 8915 total substitutions (FIG. 1A). Additional potential drivers in these subclones include RB1 S485F mutation, 17p LOH, PDE4B biallelic loss, and amplification of NCOA2 and FOXA1. RB1 S485F is not currently contained in COSMIC (20), but is predicted to be deleterious by MutationTaster2 (21), Provean (22), and the ICGC Data Portal.

We also analyzed L1 insertion events as possible contributors to resistance to chemotherapy, since previous studies have implicated L1 insertion events as the mediators of mutations, deletions, or rearrangements in the genome (14), but found none to be shared by all resistant subclones.

From the clinical timeline (FIG. 5), the first round of carboplatin/etoposide was associated with the longest (approx. 4 year) response window and appears likely to have been the round when the subclones 15, 14, 13, and 12 were eradicated. Subsequent rounds of carboplatin/etoposide provided a decrementing response, consistent with Darwinian selection of subclones resistant to carboplatin/etoposide.

Figure 2:
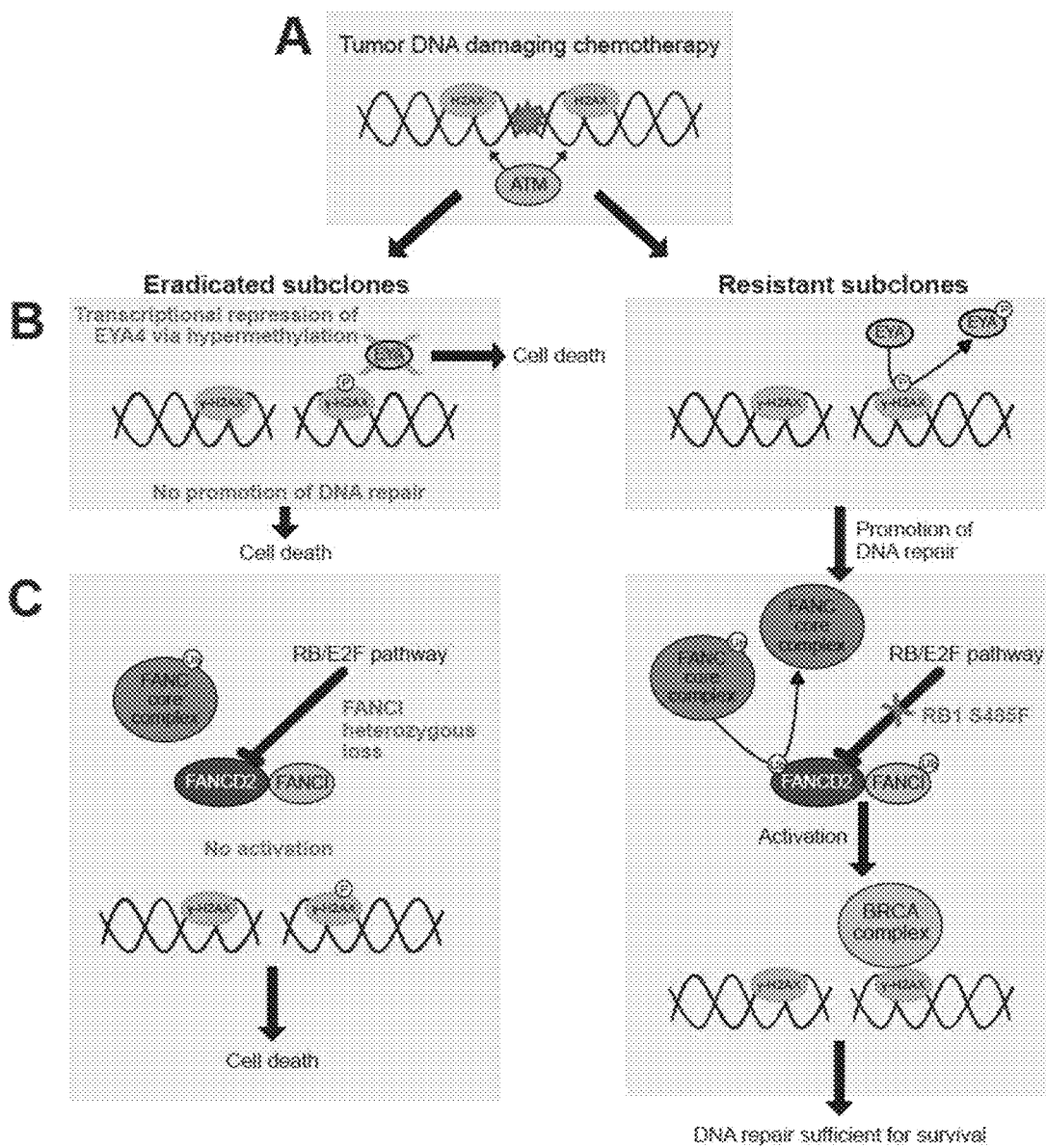
FIG. 2. Differential Subclone Eradication and Resistance (DSER) Analysis in Case A34. (A) Carboplatin and etoposide induce DNA double strand breaks, causing histone H2AX to be targeted by ATM at its 5139 phosphorylation site to form y-H2AX. (B) EYA proteins mediate the dephosphorylation of y-H2AX at the Y142 residue to promote the repair response to DNA damage. A lack of EYA protein in the eradicated subclones and consequent lack of dephosphorylation enhances cell death relative to the resistant subclones. If EYA-mediated dephosphorylation occurs, the DNA repair response proceeds. (C) Ubiquitination of the complex formed by FANCD2 and FANCI is required for activation of the BRCA DNA repair complex. If the ubiquitination is inhibited, this promotes cell death. Since the presence of FANCI is needed for FANCD2 ubiquitination, and compensatory increase in FANCD2 activity is known to occur in BRCA2-deficient tumors (12), absence (and/or reduced levels) of FANCI would likely lead to enhanced cell death in the face of DNA damaging chemotherapy. The RB/E2F pathway is implicated as a negative regulator of FANCD2 transcription. Deleterious RB1 S485F (present in all three resistant liver metastases) could lead to increased FANCD2 levels and enhanced DNA repair response, leading to subclone survival during DNA-damaging chemotherapy.

Taken together, the comparative genomic analyses of eradicated and resistant subclones in A34's metastatic cancer support the concept of high sensitivity to DNA-damaging chemotherapy due to truncal BRCA2 biallelic inactivation in all subclones, with enhanced sensitivity to chemotherapy in the eradicated subclones due to relatively deficient FANCI and EYA4 function and incrementally increasing resistance to carboplatin/etoposide conferred to resistant subclones harboring RB1 S485 mutation and other detected alterations. A visual summary of the proposed DSER analysis for A34 is shown in FIG. 2A-C.

Carboplatin and Enzalutamide Induce L1 in Prostate Cancer Cells

Figure 3A:
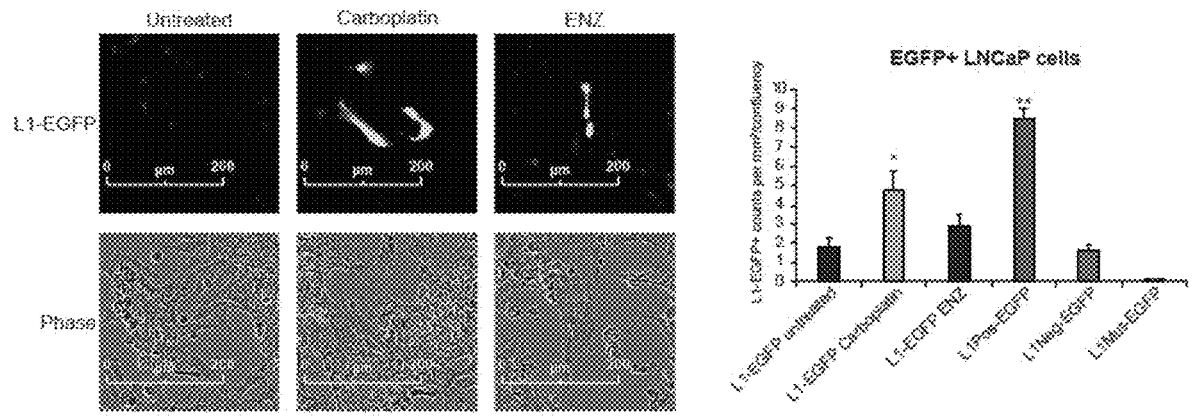
FIG. 3. Carboplatin and Enzalutamide induce L1 transposon activity in prostate cancer cells, and this activity can be blocked by azidothymidine (AZT). (A) The effects of carboplatin (5 μM) or enzalutamide (ENZ, 10 μM) on L1 activity in LNCaP prostate cancer cells analyzed using a retrotransposition L1-EGFP reporter assay and IncuCyte S3 imaging equipped with a green fluorescence channel. Representative IncuCyte cell images are shown for untreated, ENZ, and carboplatin exposed LNCaP cells with green channel only (L1-EGFP) and phase contrast. The control plasmids used included two negative controls (L1Neg-EGFP and L1Mut-EGFP) and a positive control plasmid (L1Pos-EGFP). The barplot shows L1 positive EGFP+ counts per $mm^2$/confluency quantified using IncuCyte. See also FIG. 8. (B) The effects of carboplatin or ENZ on ORF1 and ORF2 mRNA expression in LNCaP, VCaP, PC-3, and 22Rv1 prostate cancer cells. (C) L1 ORF1 and ORF2 mRNA levels from pre- and post-castration xenograft samples from LuCaP 77 and LuCaP 105 (23). (D) The effects of carboplatin and azidothymidine (AZT, 50 μM) or ENZ and AZT alone and in combination for 5 and 25 days on ORF1 and ORF2 expression in LNCaP cells and for 5 days in VCaP cells. Asterisks indicate significant difference between treatment conditions based on t-test (*, $p<0.05$; , $p<0.01$; *, $p<0.001$).
Figure 3B:
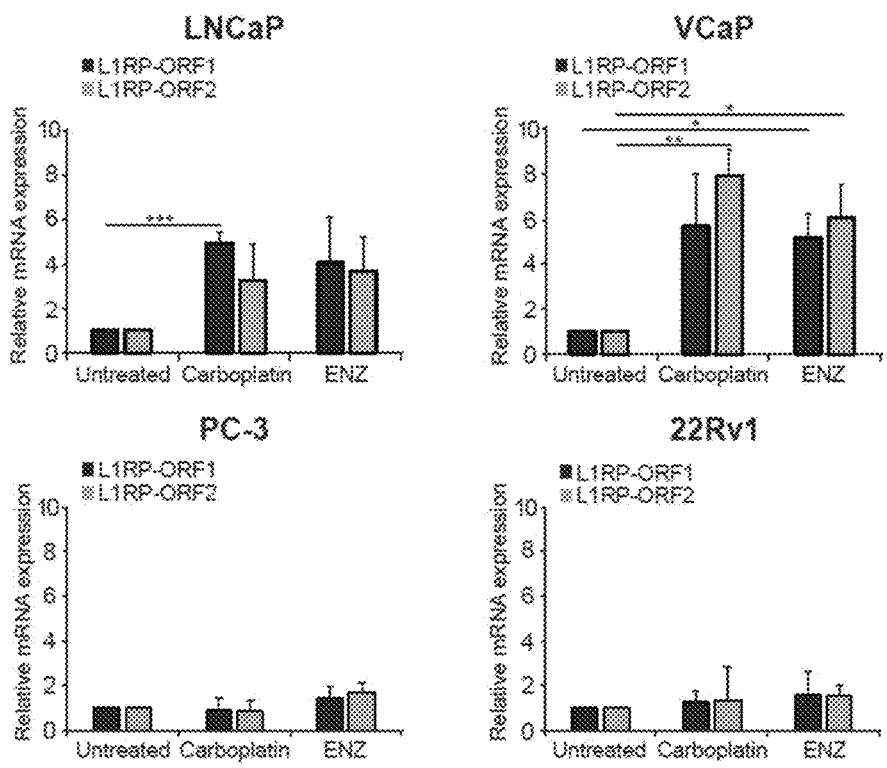
Figure 8A:
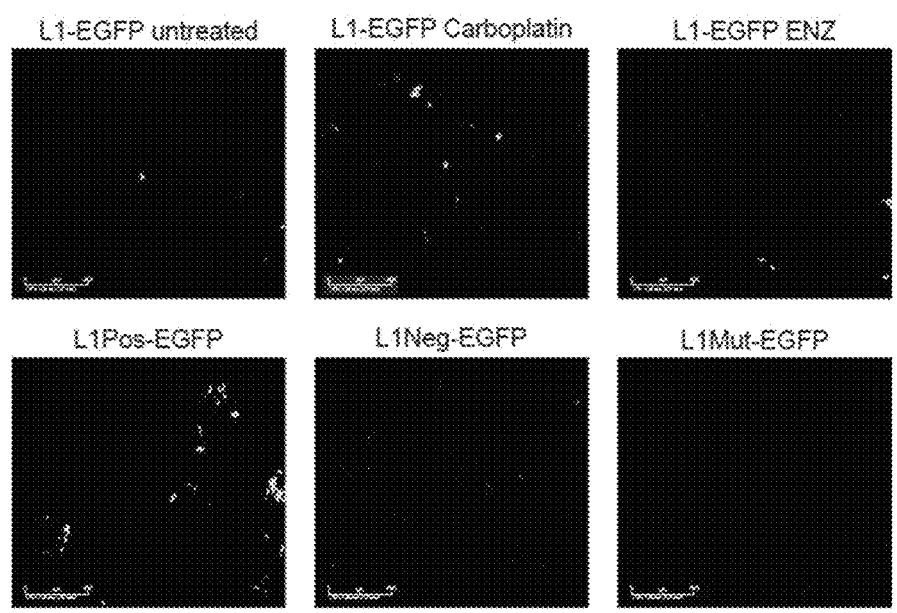
FIG. 8. LNCaP L1 response to carboplatin and enzalutamide exposure including image processing details. (A) The effects of carboplatin (5 μM) or enzalutamide (ENZ, 10 μM) on L1 activity in LNCaP prostate cancer cells analyzed using a retrotransposition L1-EGFP reporter assay and IncuCyte S3 imaging system equipped with a green fluorescence channel. The control plasmids used included two negative controls (L1Neg-EGFP) and (L1Mut-EGFP) and a positive control plasmid (L1Pos-EGFP). (B) Representative IncuCyte cell images and visualized image processing calculations used in L1 activity assays in LNCaP prostate cancer cells. Separate images are shown for untreated, carboplatin, and ENZ exposed LNCaP cells with green channel only (L1-EGFP), phase contrast only, and phase contrast+L1-EGFP, as well as for the masking of the individual green cells "L1-EGFP count mask" (light gray mask) and "Phase continency and L1-EGFP count mask" (dark gray mask). See Methods.
Figure 8B:
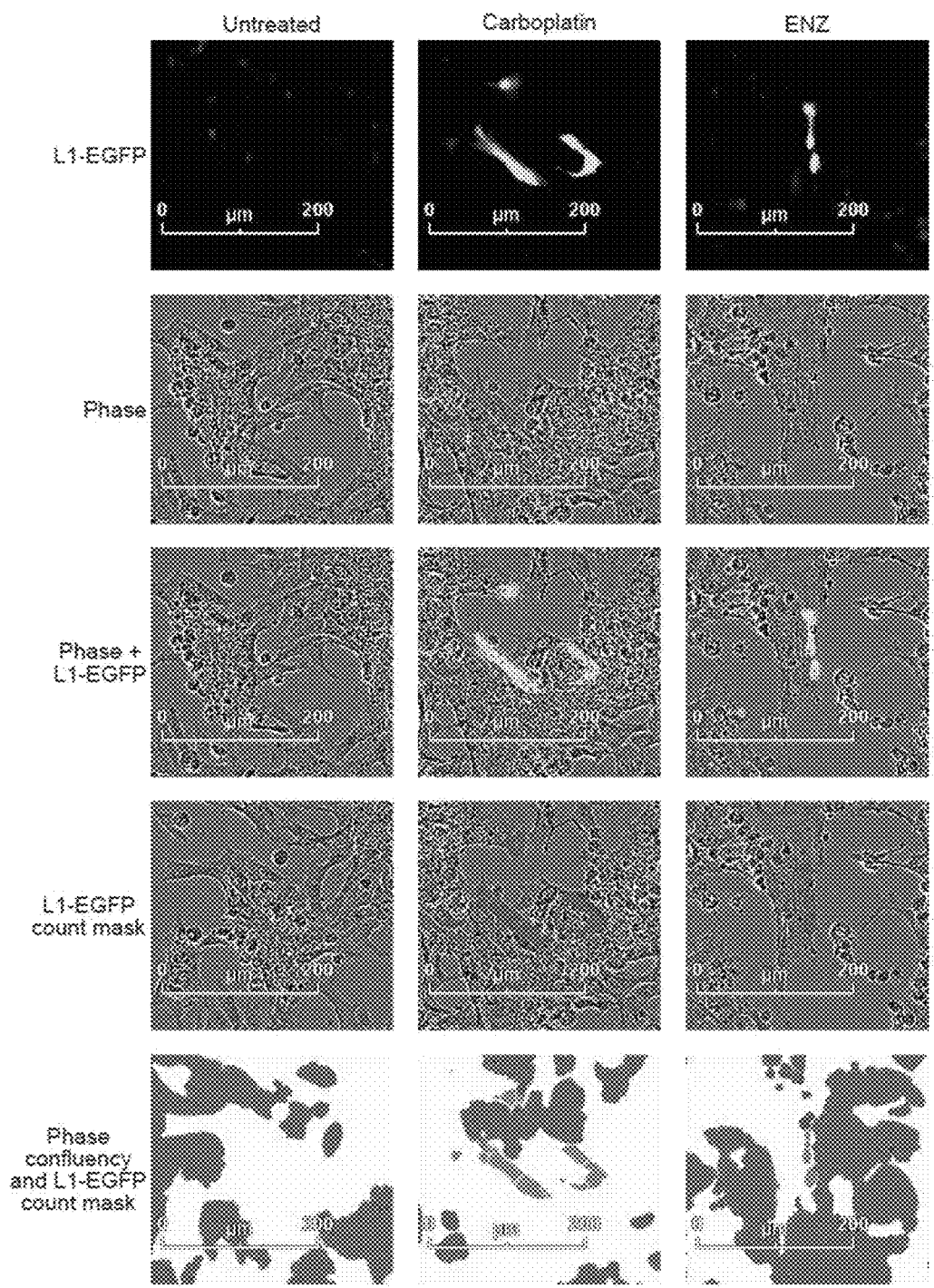

Since the pedigree of somatic L1 transposon integration in A34 metastatic cancer cells is substantially different in eradicated and resistant subclones and may be associated with differences in response to chemotherapy, we hypothesized that L1 activity is triggered by androgen deprivation or chemotherapy itself. To test this hypothesis, we exposed prostate cancer cell lines to carboplatin or enzalutamide (ENZ) and studied L1 retrotransposon activation using a retrotransposition L1-EGFP reporter assay (FIG. 3A, FIG. 8A-B). L1 retrotransposition indicated by green fluorescence appeared in LNCaP prostate cancer cells 5 days after commencement of exposure to carboplatin (FIG. 3A). With the same assay, exposure of LNCaP to ENZ showed a relative increase in L1-EGFP reporter, below statistical significance relative to control cells (FIG. 3A). We then examined L1 ORF1 and ORF2 mRNA levels in untreated, 5-day carboplatin-treated, and 5-day enzalutamide-treated LNCaP, VCaP, PC-3 and 22Rv1 cells measured by qPCR. Carboplatin induced an approximately 4-fold increase in ORF1 and ORF2 expression in LNCaP cells (p=0.004 for ORF1 and p=0.139 for ORF2, t-test) and a 7-fold increase in expression in VCaP cells (p=0.073 for ORF1 and p=0.009 for ORF2, t-test), but not in PC-3 and 22Rv1 prostate cancer cells (FIG. 3B). Notably, ENZ induced ORF1 and ORF2 expression by 5.5-fold only in VCaP cells (p=0.022 for ORF1 and p=0.026 ORF2, t-test) (FIG. 3B). These findings taken together with the L1 insertion events observed in A34 suggest that induction of L1 transposon activity by chemotherapy and/or androgen-deprivation therapy may be a contributor to genomic heterogeneity in cancer cell populations harbored in individual patients' tumors.

Figure 3C:
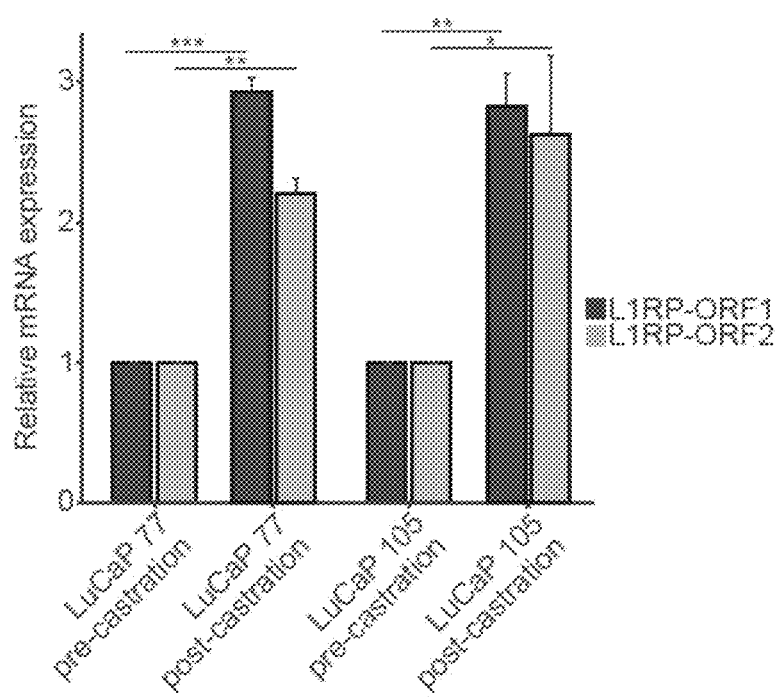
Figure 9A:
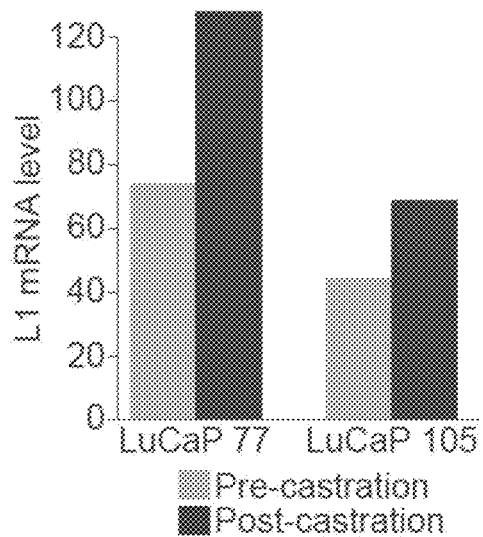
FIG. 9. Further validation of L1 activation and suppression. (A) L1 mRNA levels from pre- and post-castration samples from LuCaP 77 and LuCaP 105 (16). The y-axis shows the number of reads mapping to the 146 putatively retrotransposition active L1 elements with intact ORF1 and ORF2 from L1Base2, divided by million total aligned reads to the human genome in each sample. (B) L1 mRNA levels from head and neck squamous cell carcinoma cell line SCC25 samples treated with PBS or cetuximab in a time-series for 11 weeks (17). The y-axis shows the number of reads mapping to the 146 putatively retrotransposition active L1 elements with intact ORF1 and ORF2 from L1Base2, divided by million total aligned reads to the human genome in each sample. L1 mRNA levels are significantly different between cetuximab- and PBS-treated samples during the first five weeks of treatment (p=0.023, paired t-test). (C) Azidothymidine (AZT) blocks L1 transposon activity in the L1-EGFP reporter assay performed on LNCaP cells. (D) Western blot of L1 ORF1 protein in LNCaP cells when treated with carboplatin, azidothymidine (AZT), or both. Asterisks indicate significant differences between treatment conditions based on t-test (*, $p<0.05$; , $p<0.01$; *, $p<0.001$).
Figure 9B:
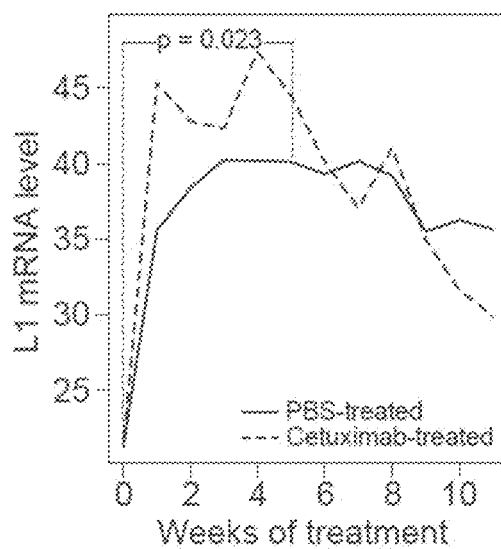

To test if L1 induction is also occurring in tumor tissues as a result of anti-androgen treatment, we examined L1 ORF1 and ORF2 mRNA levels using qPCR in patient derived LuCaP xenograft models, expanded in intact and castrate mice (LuCaP 77 and 105) (23). Castration resulted in an approximately 3-fold increase in ORF1 and ORF2 expression in both xenografts (p<0.001 for ORF1 and p=0.002 for ORF2 in LuCaP 77, p=0.005 for ORF1 and p=0.037 for ORF2 in LUCaP 105)(FIG. 3C), consistent with the cell line data. In a complementary approach, we additionally quantified L1 expression (see Methods) from previously published RNA-seq data from the same xenograft models (24) where castrated mice had higher levels of L1 mRNA (FIG. 9A). We also analyzed previously published data from a head and neck cancer cell line SCC25 treated with PBS or with cetuximab for 11 weeks (25) and examined transcriptomically once per week. Cetuximab-treated cells showed higher L1 mRNA levels during the first five weeks of treatment (p=0.023, paired t-test) (FIG. 9B). Taken together, these results suggest that L1 activation under stress may be a common phenomenon in cancer.

Figure 3D:
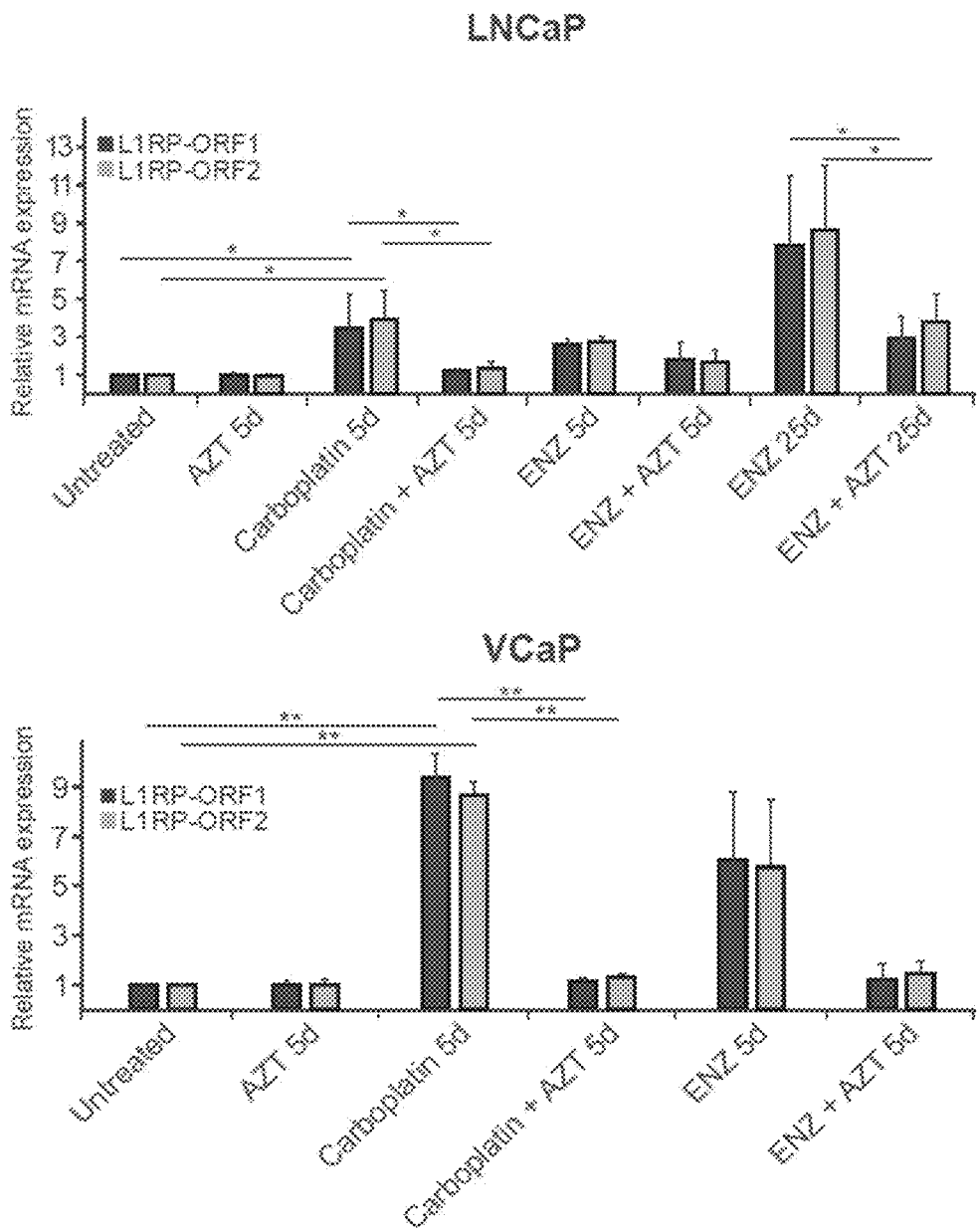
Figure 9C:
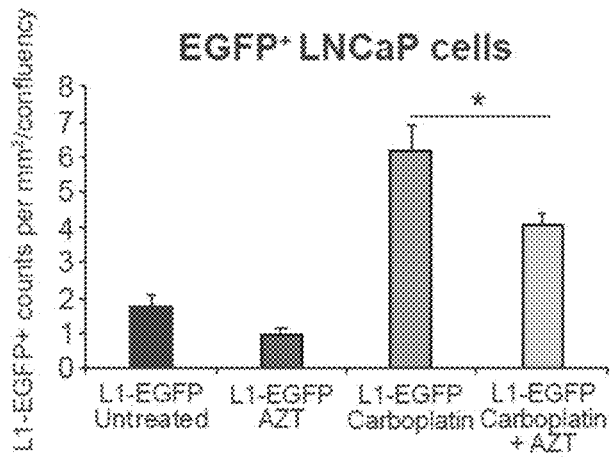
Figure 9D:
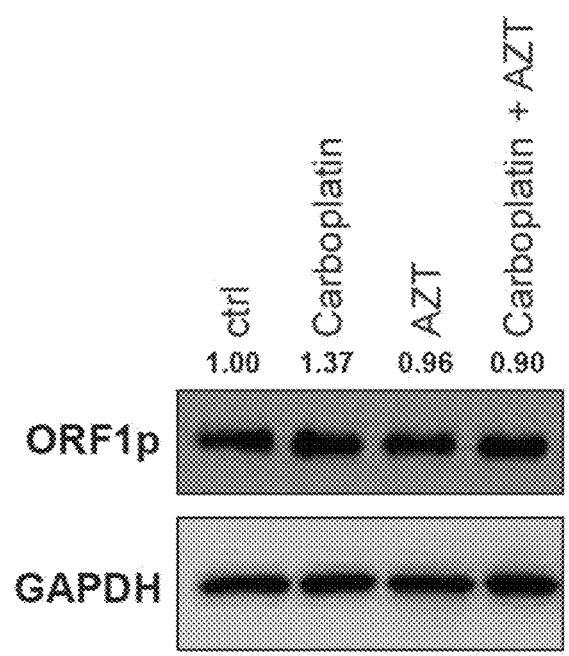

Antiretroviral Drug Azidothymidine (AZT) Reverses Treatment-Induced L1 Activity in Prostate Cancer Cells As an antiretroviral compound, nucleoside analogue reverse transcriptase inhibitor (nRTI) azidothymidine (AZT) has previously been reported to suppress L1 retrotransposition in HeLa cells (26). We hypothesized that AZT may be able to reduce carboplatin- and ENZ-induced L1 activity. Thus, we explored the effect of AZT on both ORF1 and ORF2 expression alone and in combination with carboplatin or ENZ in LNCaP and VCaP prostate cancer cells in vitro. In addition, as ENZ-induced ORF1 and ORF2 expression was only seen in VCaP cells after a 5-day delay, we included a longer 25-day exposure period for ENZ and AZT alone and in combination in LNCaP cells to determine whether ORF1 and ORF2 expression is altered in response to acquired resistance to ENZ. Next, AZT was introduced to both LNCaP and VCaP cells alone and in combination with carboplatin or ENZ. The results revealed that while carboplatin alone induced ORF1 and ORF2 mRNA expression approximately 4-fold compared to control treated LNCaP (p=0.036 for ORF1 and p=0.013 for ORF2, t-test) and 9-fold compared to control treated VCaP cells (p=0.004 for ORF1 and p=0.002 for ORF2, t-test), AZT alone did not have any significant effect on basal ORF1 and ORF2 mRNA expression (FIG. 3D). Moreover, combined administration of carboplatin and AZT kept the ORF1 and ORF2 levels at the basal level and no induction of ORF1 or ORF2 expression was detected in the combination treated LNCaP (p=0.045 for ORF1 and p=0.017 for ORF2, t-test) or VCaP cells (p=0.004 for ORF1 and p=0.001 for ORF2, t-test) (FIG. 3D). Interestingly, while no significant changes of ENZ on ORF1 and ORF2 mRNA expression were seen after a 5-day delay in LNCaP cells, a longer 25-day ENZ incubation significantly induced ORF1 and ORF2 mRNA expression by 8-fold in LNCaP cells (p=0.014 for ORF1 and p=0.007 for ORF2, t-test). Further, addition of AZT reduced the ENZ-induced ORF1 and ORF2 mRNA expression by 60% leading to only 3-fold ORF1 and ORF2 induction in ENZ and AZT combination-treated LNCaP cells (p=0.038 for ORF1 and p=0.029 for ORF2, t-test) (FIG. 3D). AZT was also able to block L1 transposon activity in the L1-EGFP reporter assay (p<0.05, t-test) FIG. 9C). Additionally, AZT blocked the ENZ induced ORF1 and ORF2 mRNA expression in VCaP cells (FIG. 3D). On the protein level, carboplatin treatment of LNCaP cells significantly increased the level of L1 ORF1p produced by the cells, while further addition of AZT returned ORF1p levels to normal (FIG. 9D). These results suggest that AZT prevents carboplatin- and ENZ-induced ORF1 and ORF2 expression and could be a modulator of cancer genome heterogeneity induction by L1 activity in cancer cells in patients during therapy.

Discussion

By combining deep longitudinal analysis of clinical, liquid biopsy, and tumor genomic data in patient A34's metastatic prostate cancer, we identified what we believe to be the first genomically documented case of differential cancer subclone eradication and resistance in a solid tumor (2). In the current study, we sought to delve deeper, to identify potential underlying causes of differential susceptibility to therapy, and to test the idea that Differential Subclone Eradication and Resistance analysis (DSER) could provide a highly informative intermediate step toward effective precision cancer medicine. DSER can be defined as a direct comparison of molecular attributes of pre- and post-treatment cancer subclones eradicated by and resistant to therapy to identify molecular targets for therapeutic conversion of resistant subclones to an eradicable state.

Our results revealed that in the eradicated cancer subclones of patient A34, the already-reduced DNA damage repair capacity provided by BRCA2 biallelic loss may have been potentiated by reduced activity of EYA4 and/or FANCI. The resistant subclones may have survived chemotherapy because of a RB1 S485F mutation. As a precision-medicine hypothesis-generating system, we believe this type of analysis could form a new and much-needed bridge to more rapid progress in precision medicine, both in individual patients and in advancing mechanistic understanding in general. In patient A34 or cells in vitro mimicking A34, could the addition of drugs blocking the FANCD2 or FANCI, and/or drugs blocking EYA4 activity force the resistant subclones to be eradicated by platinum/etoposide or DNA-repair inhibiting drugs such as olaparib? Because the root observations are in vivo and naturally developed in human, the differences observed using DSER are arguably more likely to identify useful vulnerabilities than studies starting with cell line or animal studies. Moreover, when hypotheses generated by DSER are tested in vitro and in animal studies, the power to unravel important mechanisms is likely to be substantially amplified.

How can we test the hypothesis that broadly applied DSER could accelerate progress in precision cancer medicine? The most dramatic recent advances in metastatic cancer treatment have occurred in cancers harboring DNA-repair defects (10) and in those responsive to recently developed immunotherapy methods, but these treatments typically do not cure the patient. This makes them the best place to apply DSER. The tools required to do DSER on a broad scale are relatively modest. First, whole genome-sequenced samples of tumor and blood are required prior to treatment and at the time of relapse. What can be learned about any eradicated and resistant subclones identified in the samples will be directly proportional to the quality and sufficiency of the samples for integrated clinical and molecular analysis. Whether or not subclone eradication is common enough with current partially effective therapies to warrant broader expansion of a DSER approach should become evident with as few as perhaps 20 patients with each tumor-treatment type combination. This method could be added to existing clinical trials and could be a specific additional focus of existing large studies of metastatic cancer such as those reported by Robinson et al (27) and Swanton et al (28).

Performing DSER in patient A34 caused us to ask whether L1 transposon activation itself is a targetable source of cancer genomic heterogeneity leading to differential sensitivity to therapy.

Our results are to our knowledge the first to show that either carboplatin or enzalutamide can turn on L1 transposon machinery in cancer cells, and that this induced activation can be blocked in vitro by the antiretroviral drug AZT. We were surprised to discover that L1 activation after carboplatin occurs only after a 5-day delay in two of the four prostate cancer cell lines tested. The delay may explain why L1 activation was not detected in a previous study where osteosarcoma cells were studied immediately after cisplatin exposure (29). These findings indicate that induced L1 activity in response to stresses such as carboplatin chemotherapy or androgen deprivation may contribute to genomic heterogeneity-driven resistance to therapy in some cancers.

What remains unknown about somatic L1 induction in cancer is what initiates the initial binding of RNA Polymerase II to begin the transposition process. Our results provide a foundation for mechanistic studies of L1 induction, and could help reveal why the prevalence of somatic L1 induction varies among cancer cell types (14). In prostate cancer, we speculate that differences in driver genes and remaining Androgen Receptor (AR) response pathways could underlie the L1 inducibility shown in LNCaP/VCaP cells that is lacking in PC-3/22Rv1 cell lines.

It appears possible that in A34 L1 activity induced by carboplatin and etoposide chemotherapy could have contributed to genomic instability leading both to the eradicable and resistant subclones. Testing whether or not chemotherapy induced L1 activity is clinically important or not could be tested in vivo by comparing ctDNA response to chemotherapy in patients treated with pre-chemo suppression of L1 by AZT vs. placebo. AZT is currently included in several clinical trials in leukemia, lymphoma, and other cancers. The impact of AZT on L1 activation could be studied in samples from patients enrolled in those trials (30).

In summary, future work testing of DSER-based identification of novel cancer therapeutic targets, and deeper mechanistic studies of the role and manipulability of L1 induction in cancer evolution and therapy could accelerate progress in development of effective precision oncology.

REFERENCES

1. Ma X, Edmonson M, Yergeau D, Muzny D M, Hampton O A, Rusch M, et al. Rise and fall of subclones from diagnosis to relapse in pediatric B-acute lymphoblastic leukaemia. Nature Communications. 2015; 6:6604.
2. Woodcock D J, Riabchenko E, Taavitsainen S, Kankainen M, Gundem G, Brewer D S, et al. Prostate cancer evolution from multilineage primary to single lineage metastases with implications for liquid biopsy. Nature Communications. Nature Publishing Group; 2020; 11:5070.
3. Tubio J M C, Li Y, Ju Y S, Martincorena I, Cooke S L, Tojo M, et al. Mobile DNA in cancer. Extensive transduction of nonrepetitive DNA mediated by L1 retrotransposition in cancer genomes. Science. 2014; 345:1251343.
4. Kimberland M L, Divoky V, Prchal J, Schwahn U, Berger W, Kazazian H H. Full-length human L1 insertions retain the capacity for high frequency retrotransposition in cultured cells. Hum Mol Genet. 1999; 8:1557-60.
5. Ostertag E M, Kazazian H H. Twin Priming: A Proposed Mechanism for the Creation of Inversions in L1 Retrotransposition. Genome Res. 2001; 11:2059-65.
6. Faulkner G J, Billon V. L1 retrotransposition in the soma: a field jumping ahead. Mobile DNA. 2018; 9:22.
7. Liao Y, Smyth G K, Shi W. featureCounts: an efficient general purpose program for assigning sequence reads to genomic features. Bioinformatics. 2014; 30:923-30.
8. Gundem G, Van Loo P, Kremeyer B, Alexandrov L B, Tubio J M C, Papaemmanuil E, et al. The evolutionary history of lethal metastatic prostate cancer. Nature. 2015; 520:353-7.
9. Pomerantz M M, Spisak S, Jia L, Cronin A M, Csabai I, Ledet E, et al. The association between germline BRCA2 variants and sensitivity to platinum-based chemotherapy among men with metastatic prostate cancer. Cancer. 2017; 123:3532-9.
10. de Bono J, Mateo J, Fizazi K, Saad F, Shore N, Sandhu S, et al. Olaparib for Metastatic Castration-Resistant Prostate Cancer. N Engl J Med. 2020; 382:2091-102.
11. Castella M, Jacquemont C, Thompson E L, Yeo J E, Cheung R S, Huang J-W, et al. FANCI Regulates Recruitment of the F A Core Complex at Sites of DNA Damage Independently of FANCD2. PLOS Genetics. Public Library of Science; 2015; 11:e1005563.
12. Kais Z, Rondinelli B, Holmes A, O'Leary C, Kozono D, D'Andrea A D, et al. FANCD2 Maintains Fork Stability in BRCA1/2-Deficient Tumors and Promotes Alternative End-Joining DNA Repair. Cell Rep. 2016; 15:2488-99.
13. Behan F M, Iorio F, Picco G, Gonsalves E, Beaver C M, Migliardi G, et al. Prioritization of cancer therapeutic targets using CRISPR-Cas9 screens. Nature. 2019; 568: 511-6.
14. Rodriguez-Martin B, Alvarez E G, Baez-Ortega A, Zamora J, Supek F, Demeulemeester J, et al. Pan-cancer analysis of whole genomes identifies driver rearrangements promoted by LINE-1 retrotransposition. Nature Genetics. 2020; 1-14.
15. Pelechano V, Steinmetz L M. Gene regulation by antisense transcription. Nature Reviews Genetics. 2013; 14:880-93.
16. Wood E J, Chin-Inmanu K, Jia H, Lipovich L. Sense-antisense gene pairs: sequence, transcription, and structure are not conserved between human and mouse. Front Genet. 2013; 4:183.
17. Wilson I M, Vucic E A, Enfield K S S, Thu K L, Zhang Y A, Chari R, et al. EYA4 is inactivated biallelically at a high frequency in sporadic lung cancer and is associated with familial lung cancer risk. Oncogene. 2014; 33:4464-73.
18. Luo M, L1 Y, Shi X, Yang W, Zhou F, Sun N, et al. Aberrant methylation of EYA4 promotes epithelial-mesenchymal transition in esophageal squamous cell carcinoma. Cancer Science. 2018; 109:1811-24.
19. Jividen K, Kedzierska K Z, Yang C-S, Szlachta K, Ratan A, Paschal B M. Genomic analysis of DNA repair genes and androgen signaling in prostate cancer. BMC Cancer [Internet]. 2018 [cited 2021 May 28]; 18. Available from: https://www.ncbi.nlm.nih.gov/pmc/articles/PMC6180441/
20. Tate J G, Bamford S, Jubb H C, Sondka Z, Beare D M, Bindal N, et al. COSMIC: the Catalogue Of Somatic Mutations In Cancer. Nucleic Acids Res. 2019; 47:D941-7.
21. Schwarz J M, Cooper D N, Schuelke M, Seelow D. MutationTaster2: mutation prediction for the deep-sequencing age. Nature Methods. Nature Publishing Group; 2014; 11:361-2.
22. Choi Y, Sims G E, Murphy S, Miller J R, Chan A P. Predicting the Functional Effect of Amino Acid Substitutions and Indels. PLOS ONE. Public Library of Science; 2012; 7:e46688.
23. Nguyen H M, Vessella R L, Morrissey C, Brown L G, Coleman I M, Higano C S, et al. LuCaP Prostate Cancer Patient-Derived Xenografts Reflect the Molecular Heterogeneity of Advanced Disease and Serve as Models for Evaluating Cancer Therapeutics. Prostate. 2017; 77:654-71.
24. Annala M, Kivinummi K, Tuominen J, Karakurt S, Granberg K, Latonen L, et al. Recurrent SKIL-activating rearrangements in ETS-negative prostate cancer. Oncotarget. 2015; 6:6235-50.
25. Stein-O'Brien G, Kagohara L T, Li S, Thakar M, Ranaweera R, Ozawa H, et al. Integrated time course omics analysis distinguishes immediate therapeutic response from acquired resistance. Genome Med. 2018; 10:37.
26. Jones R B, Garrison K E, Wong J C, Duan E H, Nixon D F, Ostrowski M A. Nucleoside analogue reverse transcriptase inhibitors differentially inhibit human LINE-1 retrotransposition. PLoS One. 2008; 3:e1547.
27. Robinson D R, Wu Y-M, Lonigro R J, Vats P, Cobain E, Everett J, et al. Integrative clinical genomics of metastatic cancer. Nature. 2017; 548:297-303.
28. Swanton C. Take lessons from cancer evolution to the clinic. Nature. 2020; 581:382-3.
29. Farkash E A, Kao G D, Horman S R, Prak E T L. Gamma radiation increases endonuclease-dependent L1 retrotransposition in a cultured cell assay. Nucleic Acids Res. Oxford Academic; 2006; 34:1196-204.
30. Armando R G, Gomez D L M, Gomez D E. New drugs are not enough-drug repositioning in oncology: An update. Int J Oncol. 2020; 56:651-84.

Tables

TABLE 1

A34 Samples and Data studied. For each of the 10 samples used in the study, the identifiers and time of sample collection is indicated, along with sequencing data types available. Purity for samples with WGS data was inferred using the Battenberg algorithm (https://github.com/cancerit/cgpBattenberg) and purity for samples without WGS data was based on the variant allele frequency information and the DPClust algorithm as described in Woodcock et al(2). Numbers of substitutions per sample are based on the WGS data as analyzed in Gundem et al(8). WGS reference normal spleen DNA is not included in the table.

| Sample from A34 | Collection timepoint | Letter ID | Tumor Cellularity | Available sequencing data | | | Substitutions from WGS |
|---|---|---|---|---|---|---|---|
| | | | | Whole genome | Deep targeted | Methylation | |
| SacralBoneMet | 11 years prior to death | e | 0.86 | Yes | Yes | Yes | 5181 |
| Serum | 11 years prior to death | — | 0.04 | No | Yes | No | — |
| Prostate | 9 years prior to death | X | 0.70 | No | Yes | No | — |
| Prostate | 9 years prior to death | Y | 0.67 | No | Yes | No | — |
| Prostate | 9 years prior to death | Z | 0.84 | No | Yes | No | — |
| LiverMet1 | Autopsy | c | 0.84 | Yes | Yes | Yes | 12745 |
| LiverMet12 | Autopsy | d | 0.85 | Yes | Yes | Yes | 13762 |
| LiverMet3 | Autopsy | a | 0.79 | Yes | Yes | Yes | 12332 |
| Serum | Autopsy | — | 0.56 | No | Yes | Yes | — |
| Plasma | Autopsy | — | 0.63 | No | Yes | Yes | — |

TABLE 2

The qPCR primers used for L1-ORF1, L1-ORF2, FANCI, and GAPDH.

| | Forward primer | Reverse primer |
|---|---|---|
| L1-ORF1 | AGAACGCCACAAA GATACTCCTCG (SEQ ID NO: 1) | CTCTCTTCTGGCTT GTAGGGTTTCTG (SEQ ID NO: 2) |
| L1-ORF2 | AAACTGAACAACC TGCTCCTGAATG (SEQ ID NO: 3) | CTACACACTGCTTT GAATGCGTCC (SEQ ID NO: 4) |
| FANCI | CCACCTTTGGTCT ATCAGCTTC (SEQ ID NO: 5) | CAACATCCAATAGC TCGTCACC (SEQ ID NO: 6) |
| GAPDH | CGACCTGACCTGCC GTCTAGAA (SEQ ID NO: 7) | GGTGTCGCTGGTGA AGTCGAGAG (SEQ ID NO: 8) |

What is claimed is:

1. A method of identifying a molecular target for precision cancer therapy in a patient in need thereof, the method comprising:
   a) determining truncal clonal and subclonal cancer cell composition of a first sample obtained from the patient before an initial cancer treatment or treatment interval;
   b) determining truncal clonal and subclonal cancer cell composition of a second sample obtained from the patient after the initial cancer treatment or treatment interval;
   c) comparing the truncal and subclonal cancer cell compositions of the first and the second samples to distinguish a cancer cell subclone eradicated by the cancer treatment or treatment interval and a cancer cell subclone resistant to the cancer treatment or treatment interval;
   d) based on a comparison of molecular characteristics of the eradicated cancer cell subclone and the resistant cancer cell subclone, to identifying one or more molecular features of the eradicated cancer cell subclone that indicate one or more of FANCI, FANCD2, or EYA4 as one or more molecular targets for precision cancer therapy directed to converting the resistant cancer cell subclone to an eradicable cancer cell subclone; and
   e) administering the precision cancer therapy as a subsequent cancer treatment or treatment interval, after the initial cancer treatment or interval, to the patient, wherein the precision cancer therapy converts the resistant cancer cell subclone to an eradicable cancer cell subclone in the patient.

2. The method according to claim 1, wherein the step of comparing the molecular characteristics of the eradicated and resistant subclones of cancer cells comprises comparing sequence data obtained from the eradicated and resistant subclones.

3. The method according to claim 1, wherein expression of the indicated one or more of FANCI, FANCD2, or EYA4 is increased in the resistant cancer cell subclone as compared to the eradicated cancer cell subclone.

4. The method according to claim 2, wherein expression of the indicated one or more of FANCI, FANCD2, or EYA4 is increased in the resistant cancer cell subclone as compared to the eradicated cancer cell subclone.

5. The method according to claim 1, wherein the indicated one or more of FANCI, FANCD2, or EYA4 expresses a faulty protein or causes a loss of functional protein.

6. The method according to claim 2, wherein the indicated one or more of FANCI, FANCD2, or EYA4 expresses a faulty protein or causes a loss of functional protein.

7. The method according to claim 1, wherein the indicated one or more of FANCI, FANCD2, or EYA4 is a DNA repair-related gene.

8. The method according to claim 2, wherein the indicated one or more of FANCI, FANCD2, or EYA4 is a DNA repair-related gene.

9. The method according to claim 3, wherein the indicated one or more of FANCI, FANCD2, or EYA4 is a DNA repair-related gene.

10. The method according to claim 5, wherein the indicated one or more of FANCI, FANCD2, or EYA4 is a DNA repair-related gene.

11. The method according to claim 1, wherein the target-specific cancer therapeutics comprises an siRNA molecule, an shRNA molecule, a DsiRNA molecules, an artificial miRNA precursor, an antisense oligonucleotide, an antibody, a nanobody, an affibody, an aptamer, a peptide, a small molecule inhibitor or a gene editing agent such as CRISPR-Cas system.

12. The method according to claim 1, wherein converting the resistant cancer cell subclone to an eradicable subclone in the patient during the administration of the subsequent cancer treatment or treatment interval includes silencing or inhibiting expression of the indicated one or more of FANCI, FANCD2, or EYA4 in the resistant cancer cell subclone by blocking a function of a protein encoded by the one or more of FANCI, FANCD2, or EYA4.

13. The method according to claim 5, wherein converting the resistant cancer cell subclone to an eradicable subclone in the patient during the administration of the subsequent cancer treatment or treatment interval includes silencing or inhibiting expression of indicated one or more of FANCI, FANCD2, or EYA4 in the resistant cancer cell subclone by restoring a function of a protein encoded by the indicated one or more of FANCI, FANCD2, or EYA4.

14. The method according to claim 1, wherein identifying the one or more molecular features of the eradicated cancer cell subclone that indicate one or more molecular targets for the precision cancer therapy includes identifying differences in the molecular compositions of a cancer cell subclone eradicated by the cancer treatment or treatment interval and a cancer cell subclone resistant to the cancer treatment or treatment interval.

* * * * *

SEQUENCE LISTING

<160> NUMBER OF SEQ ID NOS: 16

<210> SEQ ID NO 1
<211> LENGTH: 24
<212> TYPE: DNA
<213> ORGANISM: Artificial Sequence
<220> FEATURE:
<223> OTHER INFORMATION: L1-ORF1 Forward Primer

<400> SEQUENCE: 1
agaacgccac aaagatactc ctcg                                    24

<210> SEQ ID NO 2
<211> LENGTH: 26
<212> TYPE: DNA
<213> ORGANISM: Artificial Sequence
<220> FEATURE:

<223> OTHER INFORMATION: L1-ORF1 Reverse Primer

<400> SEQUENCE: 2
ctctcttctg gcttgtaggg tttctg                                    26

<210> SEQ ID NO 3
<211> LENGTH: 25
<212> TYPE: DNA
<213> ORGANISM: Artificial Sequence
<220> FEATURE:
<223> OTHER INFORMATION: L1-ORF2 Forward Primer

<400> SEQUENCE: 3
aaactgaaca acctgctcct gaatg                                     25

<210> SEQ ID NO 4
<211> LENGTH: 24
<212> TYPE: DNA
<213> ORGANISM: Artificial Sequence
<220> FEATURE:
<223> OTHER INFORMATION: L1-ORF2 Reverse Primer

<400> SEQUENCE: 4
ctacacactg ctttgaatgc gtcc                                      24

<210> SEQ ID NO 5
<211> LENGTH: 22
<212> TYPE: DNA
<213> ORGANISM: Artificial Sequence
<220> FEATURE:
<223> OTHER INFORMATION: FANCI Forward Primer

<400> SEQUENCE: 5
ccacctttgg tctatcagct tc                                        22

<210> SEQ ID NO 6
<211> LENGTH: 22
<212> TYPE: DNA
<213> ORGANISM: Artificial Sequence
<220> FEATURE:
<223> OTHER INFORMATION: FANCI Reverse Primer

<400> SEQUENCE: 6
caacatccaa tagctcgtca cc                                        22

<210> SEQ ID NO 7
<211> LENGTH: 22
<212> TYPE: DNA
<213> ORGANISM: Artificial Sequence
<220> FEATURE:
<223> OTHER INFORMATION: GAPDH Forward Primer

<400> SEQUENCE: 7
cgacctgacc tgccgtctag aa                                        22

<210> SEQ ID NO 8
<211> LENGTH: 23
<212> TYPE: DNA
<213> ORGANISM: Artificial Sequence
<220> FEATURE:
<223> OTHER INFORMATION: GAPDH Reverse Primer

<400> SEQUENCE: 8
ggtgtcgctg gtgaagtcga gag                                       23

```
<210> SEQ ID NO 9
<211> LENGTH: 19
<212> TYPE: RNA
<213> ORGANISM: Artificial Sequence
<220> FEATURE:
<223> OTHER INFORMATION: siRNA

<400> SEQUENCE: 9
acagaguggu gacgagcua                                              19

<210> SEQ ID NO 10
<211> LENGTH: 19
<212> TYPE: RNA
<213> ORGANISM: Artificial Sequence
<220> FEATURE:
<223> OTHER INFORMATION: siRNA

<400> SEQUENCE: 10
gcagaaagaa auagcgucu                                              19

<210> SEQ ID NO 11
<211> LENGTH: 19
<212> TYPE: RNA
<213> ORGANISM: Artificial Sequence
<220> FEATURE:
<223> OTHER INFORMATION: siRNA

<400> SEQUENCE: 11
gauacuuguc cuucggaaa                                              19

<210> SEQ ID NO 12
<211> LENGTH: 19
<212> TYPE: RNA
<213> ORGANISM: Artificial Sequence
<220> FEATURE:
<223> OTHER INFORMATION: siRNA

<400> SEQUENCE: 12
acgaagaccu agaugauau                                              19

<210> SEQ ID NO 13
<211> LENGTH: 19
<212> TYPE: RNA
<213> ORGANISM: Artificial Sequence
<220> FEATURE:
<223> OTHER INFORMATION: siRNA

<400> SEQUENCE: 13
ugguuuacau gucgacuaa                                              19

<210> SEQ ID NO 14
<211> LENGTH: 19
<212> TYPE: RNA
<213> ORGANISM: Artificial Sequence
<220> FEATURE:
<223> OTHER INFORMATION: siRNA

<400> SEQUENCE: 14
ugguuuacau guuguguga                                              19

<210> SEQ ID NO 15
<211> LENGTH: 18
<212> TYPE: RNA
<213> ORGANISM: Artificial Sequence
<220> FEATURE:
<223> OTHER INFORMATION: siRNA
```

```
<400> SEQUENCE: 15
gguuuacaug uuuucuga                                                  18

<210> SEQ ID NO 16
<211> LENGTH: 19
<212> TYPE: RNA
<213> ORGANISM: Artificial Sequence
<220> FEATURE:
<223> OTHER INFORMATION: siRNA

<400> SEQUENCE: 16
ugguuuacau guuuuccua                                                 19
```